(12) United States Patent
Abdou

(10) Patent No.: US 8,906,092 B2
(45) Date of Patent: Dec. 9, 2014

(54) SPINOUS PROCESS FIXATION DEVICES AND METHODS OF USE

(76) Inventor: Samy Abdou, San Diego, CA (US)

(*) Notice: Subject to any disclaimer, the term of this patent is extended or adjusted under 35 U.S.C. 154(b) by 242 days.

(21) Appl. No.: 13/357,509

(22) Filed: Jan. 24, 2012

(65) Prior Publication Data

US 2012/0191135 A1 Jul. 26, 2012

Related U.S. Application Data

(60) Provisional application No. 61/461,839, filed on Jan. 24, 2011.

(51) Int. Cl.
*A61F 2/44* (2006.01)
*A61B 17/70* (2006.01)

(52) U.S. Cl.
CPC .......... *A61B 17/7065* (2013.01); *A61B 17/7068* (2013.01)
USPC ........................................ 623/17.11; 606/248

(58) Field of Classification Search
CPC ............ A61B 17/7068; A61B 17/7067; A61B 17/7064; A61B 17/025; A61B 17/702; A61B 17/809; A61F 2002/30841; A61F 2002/448; A61F 2/44
USPC ...................... 606/246–249; 623/17.11, 17.16
See application file for complete search history.

(56) References Cited

U.S. PATENT DOCUMENTS

| | | | |
|---|---|---|---|
| 7,753,938 B2 | 7/2010 | Aschmann et al. | |
| 8,075,593 B2 | 12/2011 | Hess | |
| 8,142,479 B2 | 3/2012 | Hess | |
| 2008/0195152 A1* | 8/2008 | Altarac et al. | 606/249 |
| 2010/0234889 A1* | 9/2010 | Hess | 606/249 |
| 2011/0009970 A1* | 1/2011 | Puno | 623/17.16 |
| 2011/0054531 A1* | 3/2011 | Lamborne et al. | 606/249 |
| 2012/0041272 A1* | 2/2012 | Dietze et al. | 600/231 |

OTHER PUBLICATIONS

Denis, F. "The three column spine and its significance in the classification of acute thoracolumbar spinal injuries" Spine Nov.-Dec. 1983; 8(8):817-831.
Holland, NR., *Intraoperative electromyography, during thoracolumbar spinal surgery*, Spine Sep. 1, 1998:23 (17): 1915-1922.
Wood, MJ, et al., *Improving accuracy and reducing radiation exposure in minimally invasive lumbar interbody fusion*, J Neurosurg Spine. May 2010: 12(5): 533-539.
Frank Netter. Atlas of Human Anatomy 3rd Edition, Icon Learning Systems, Tegerboro, New Jersey.

* cited by examiner

*Primary Examiner* — Mary Hoffman
*Assistant Examiner* — Tara Carter
(74) *Attorney, Agent, or Firm* — Gazdzinski & Associates, PC

(57) ABSTRACT

Devices and methods for the treatment of abnormal spinal stability and stenosis of the spinal canal by the implantation of orthopedic devices between skeletal segments. In one embodiment, a device is disclosed to rigidly fixate the spinous processes of two vertebral bones relative one another. A first member of the device is advanced across an interspinous space, rotated, and/or advanced onto the contralateral side of the spinous processes. A second member of the device is also advanced onto the ipsilateral side of the spinous processes and forcibly captures the spinous processes between the first and second members. A protrusion extends from the first and/or second devices configured to embed into the bone of the spinous processes thereby increasing the immobilization strength of the device. The implant may be further configured to contain a bone forming material to form a fusion between the first and the second vertebral bones.

21 Claims, 37 Drawing Sheets

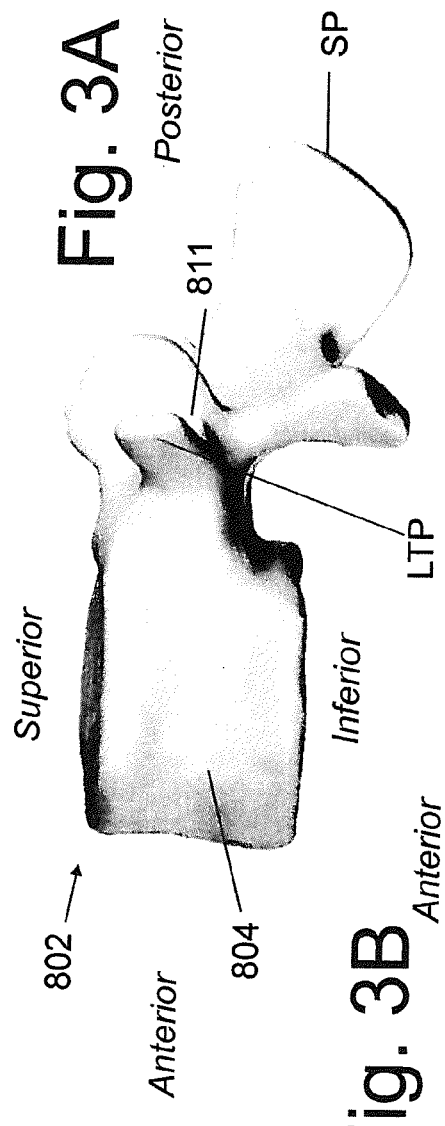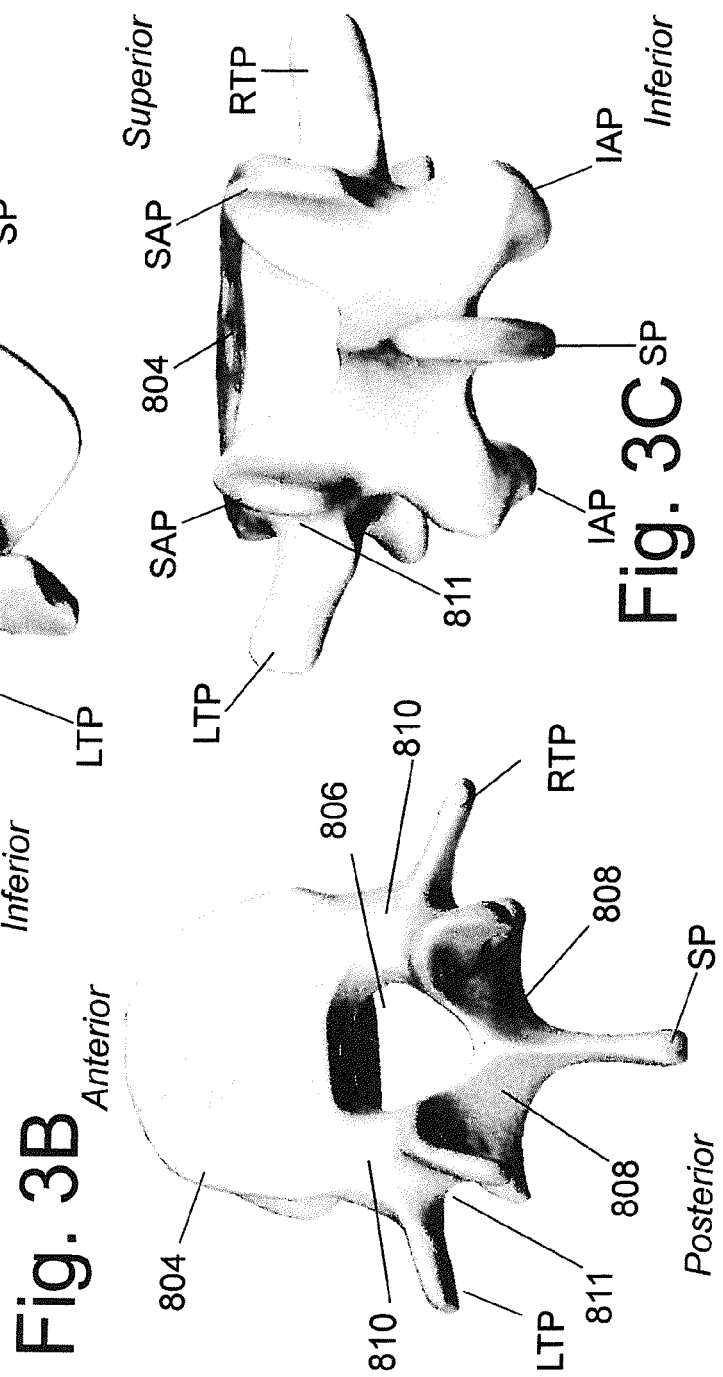

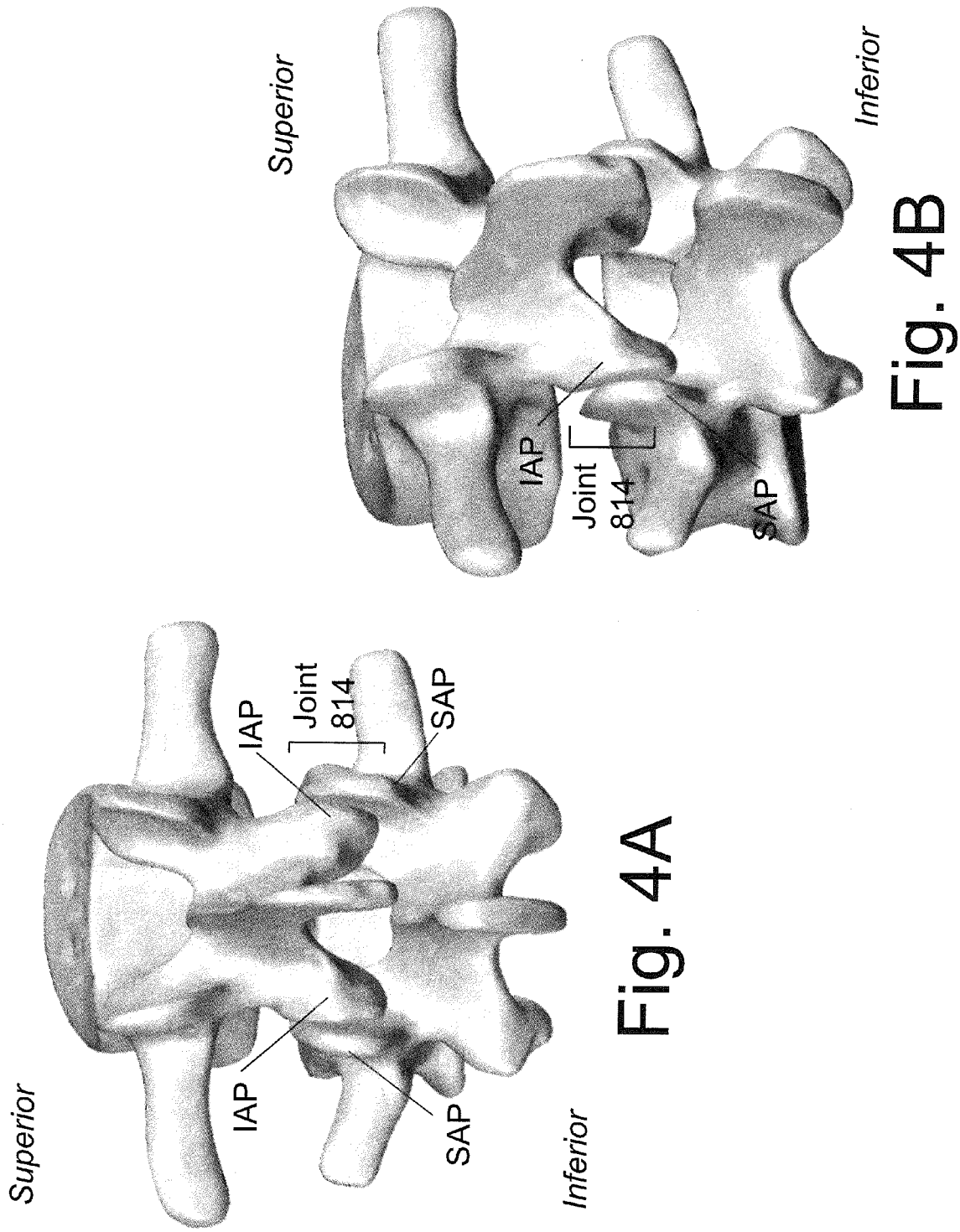

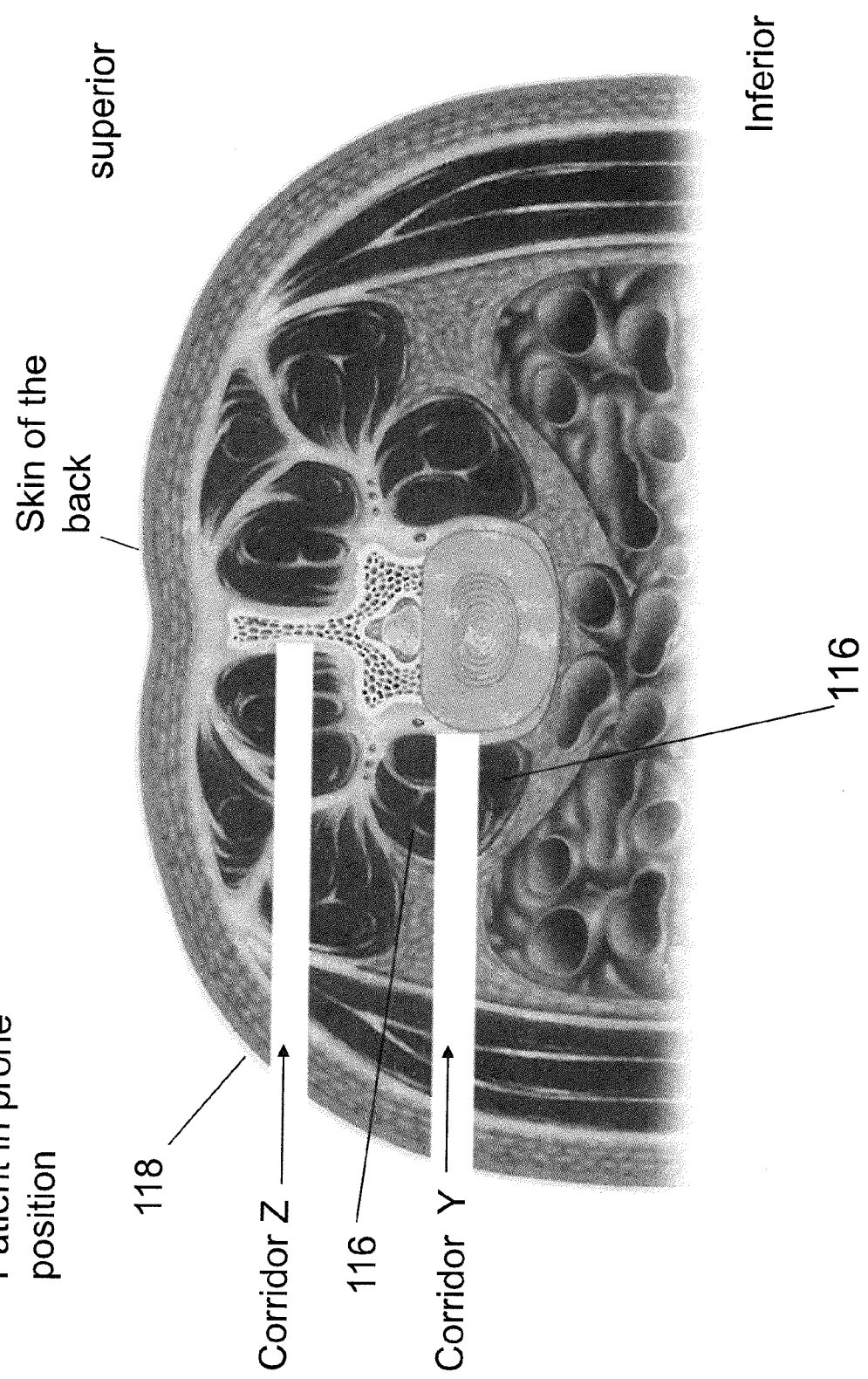

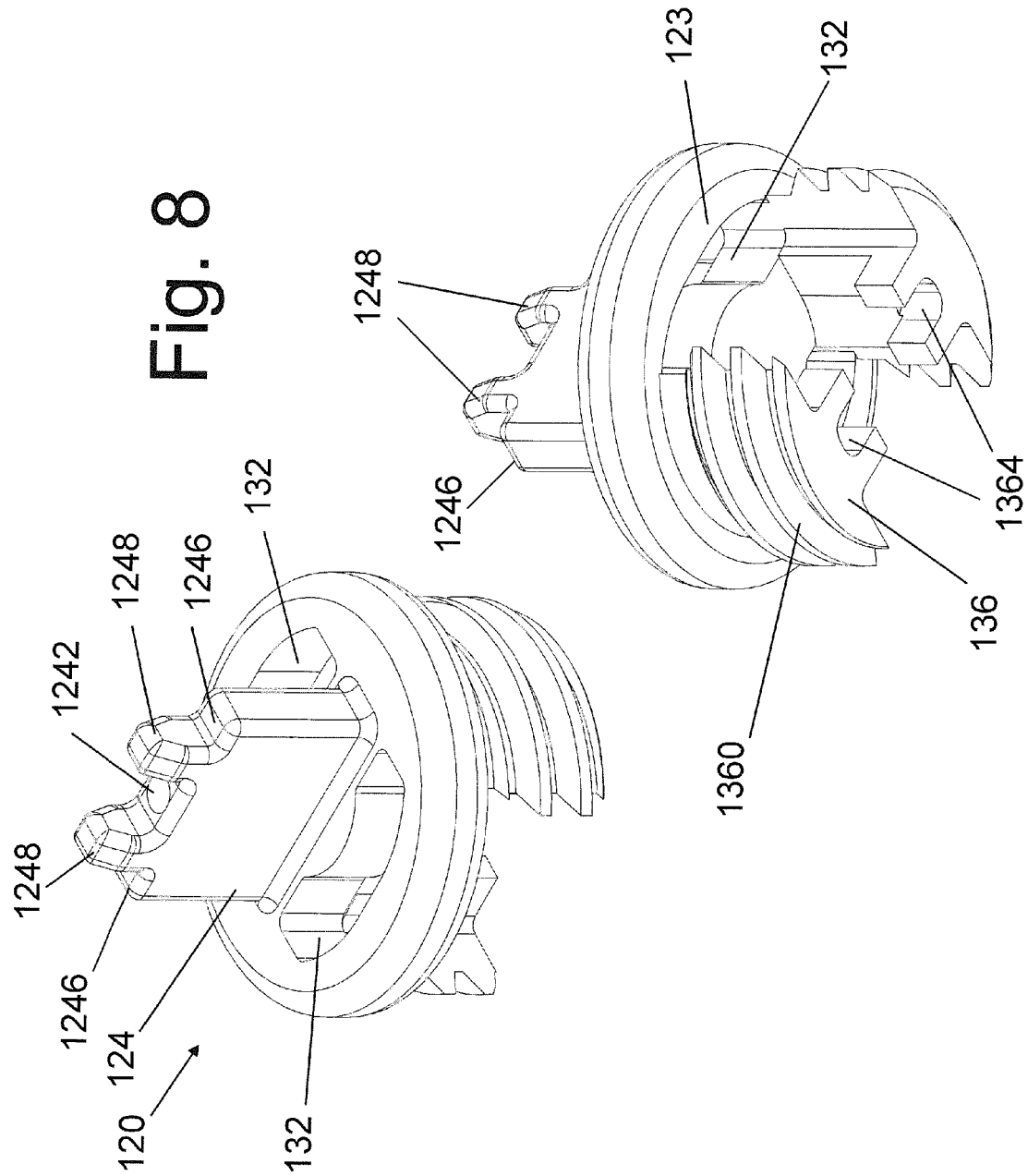

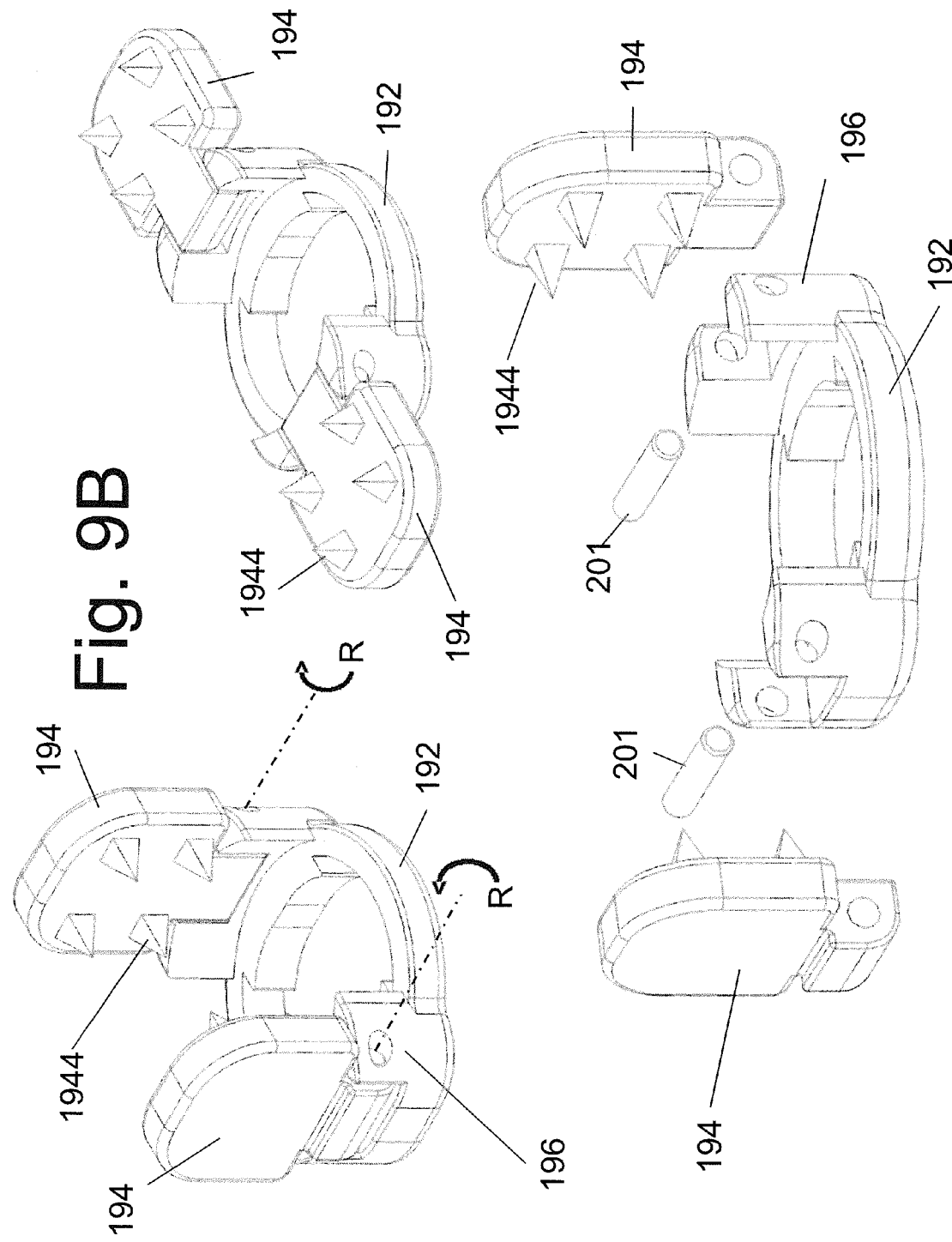

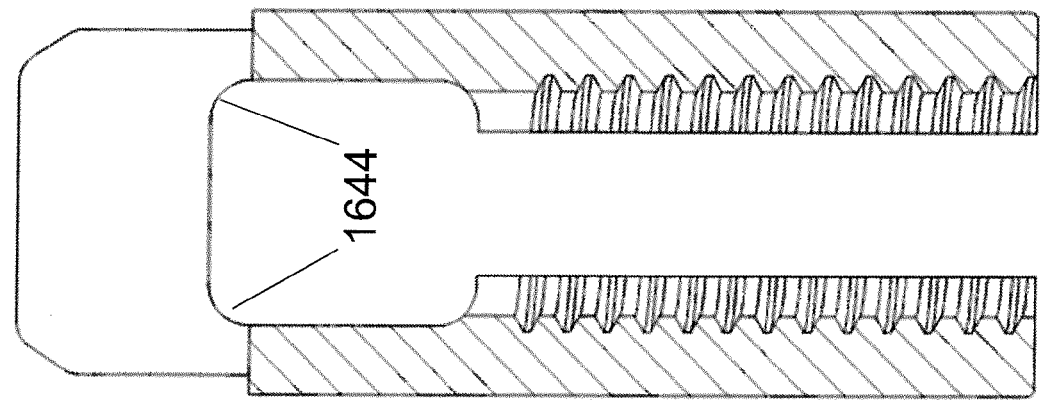
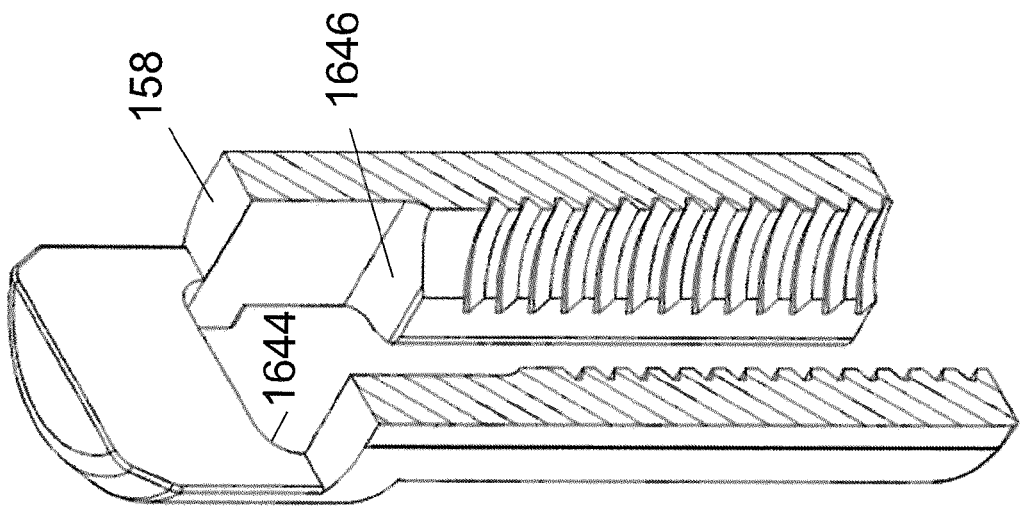
Fig. 12

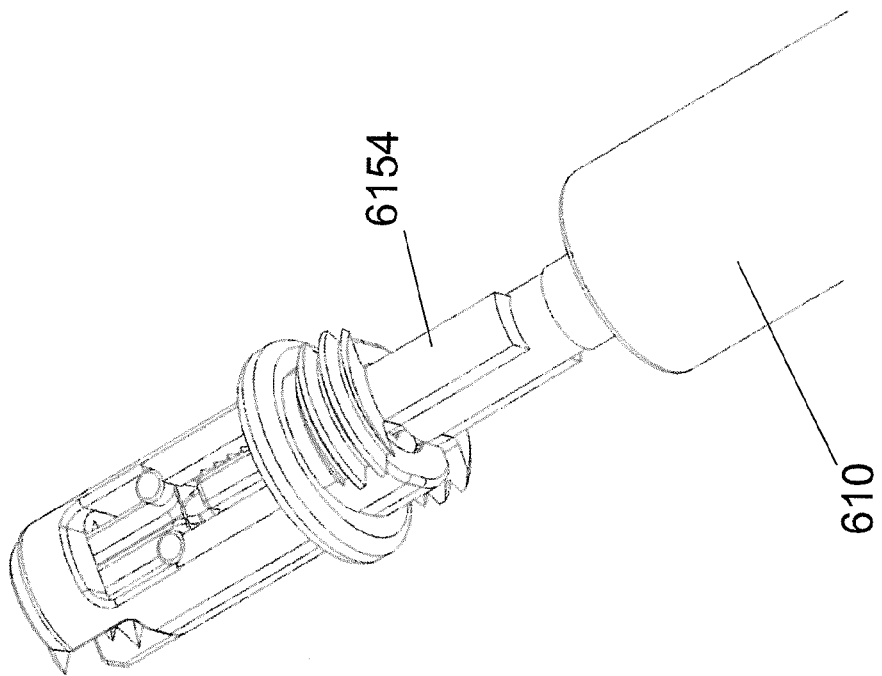
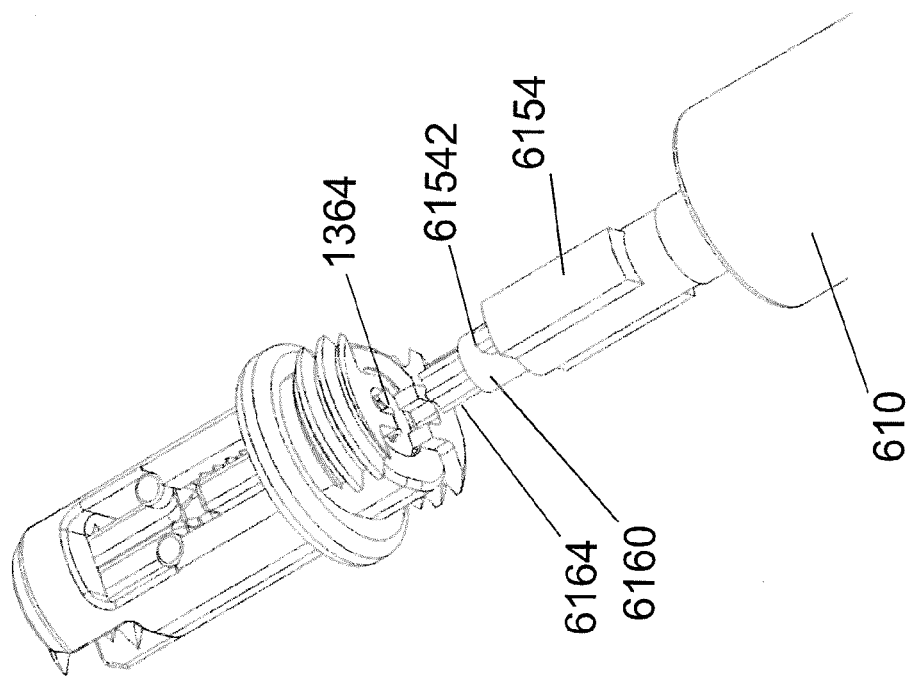
Fig. 23

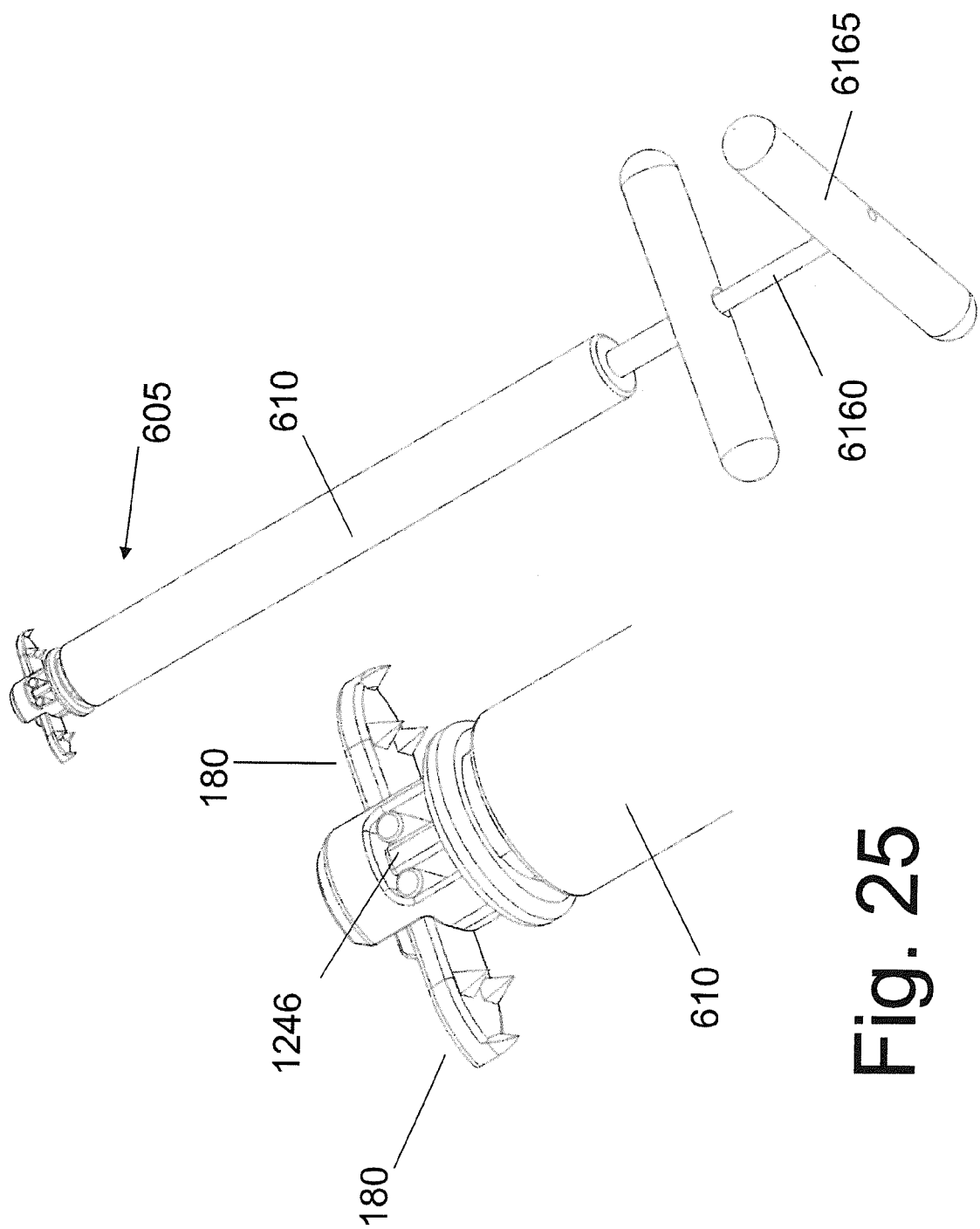

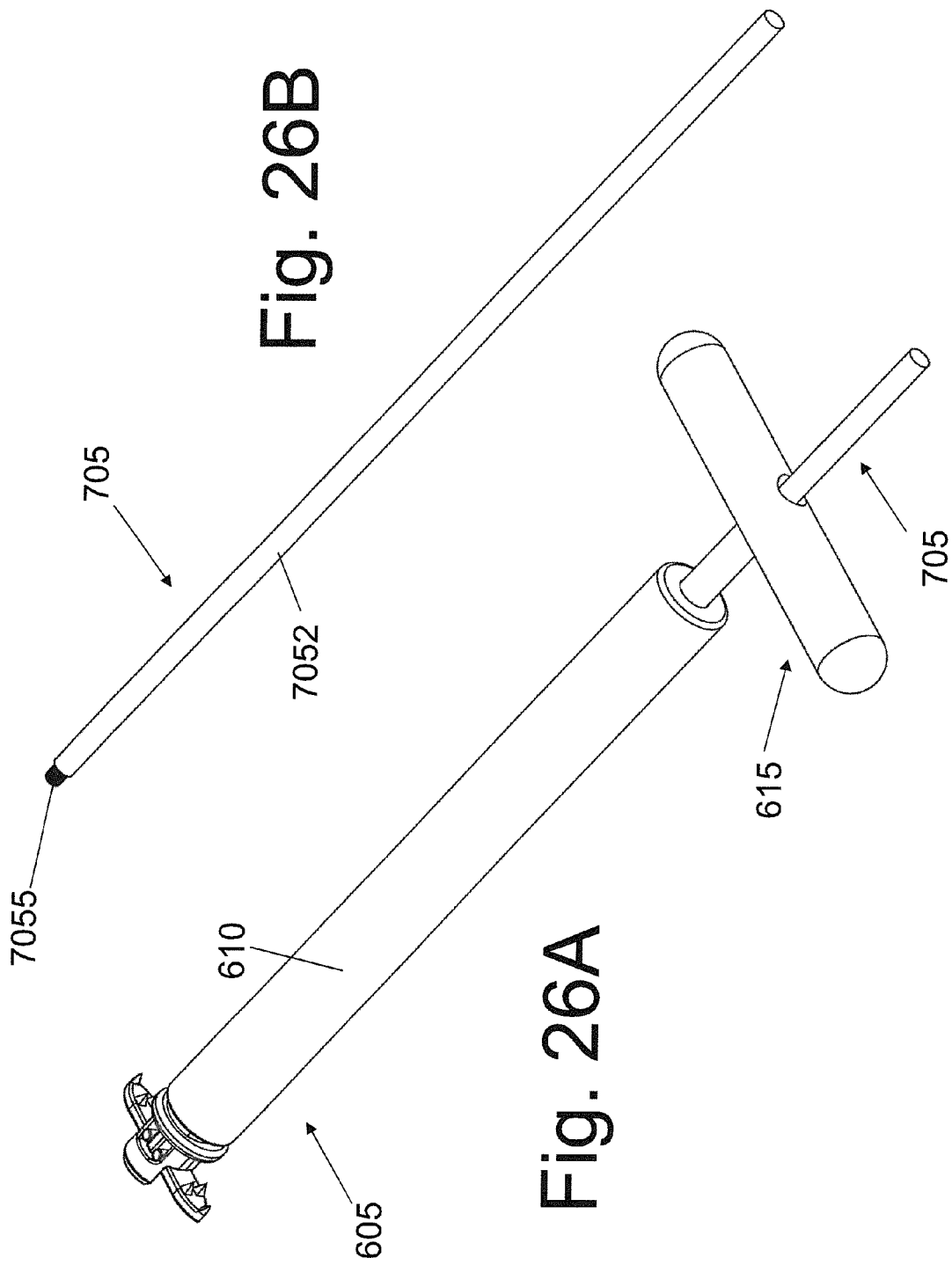

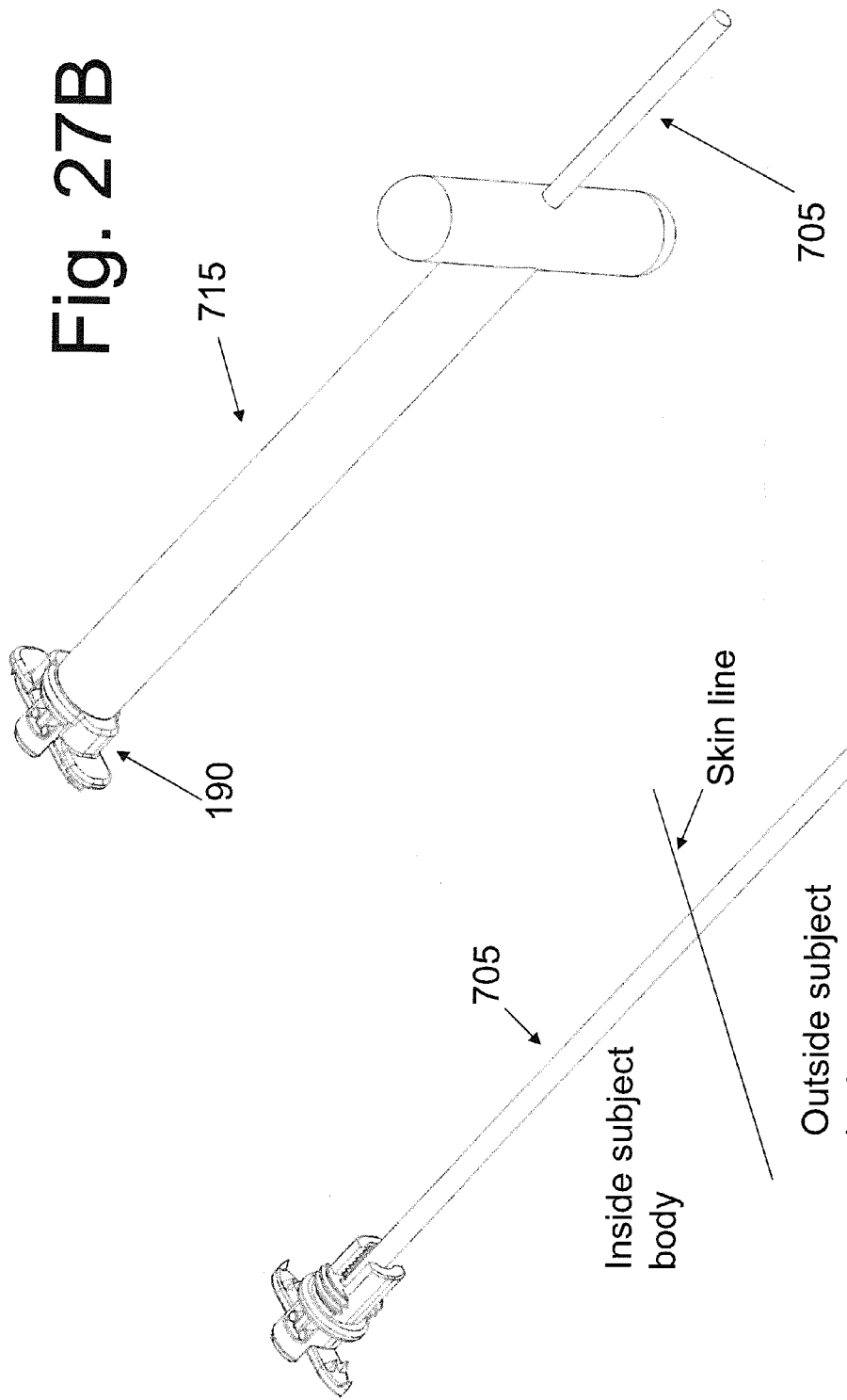

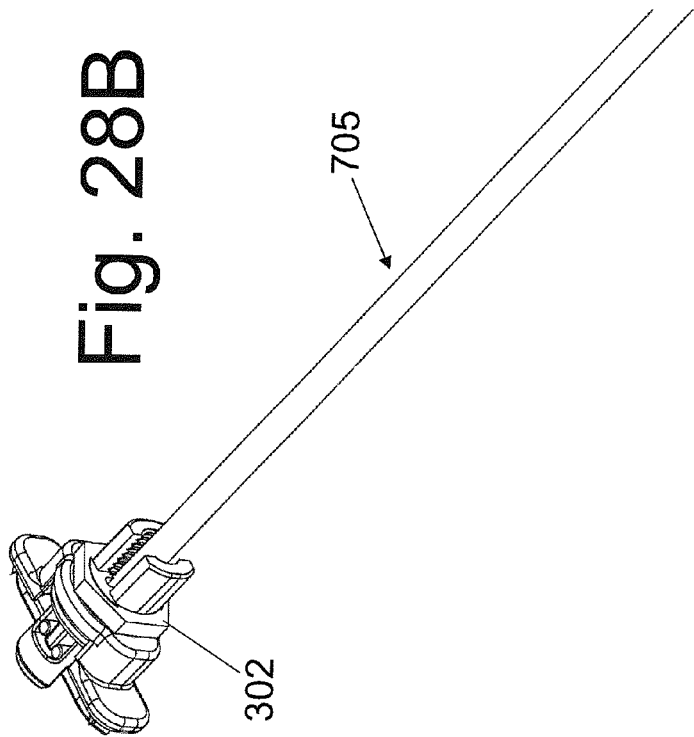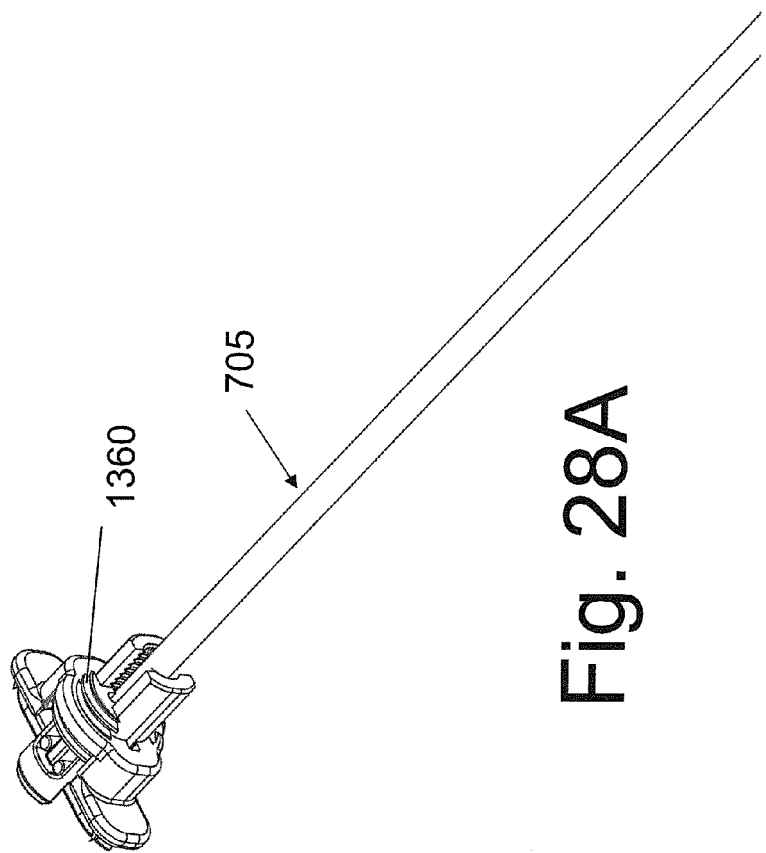

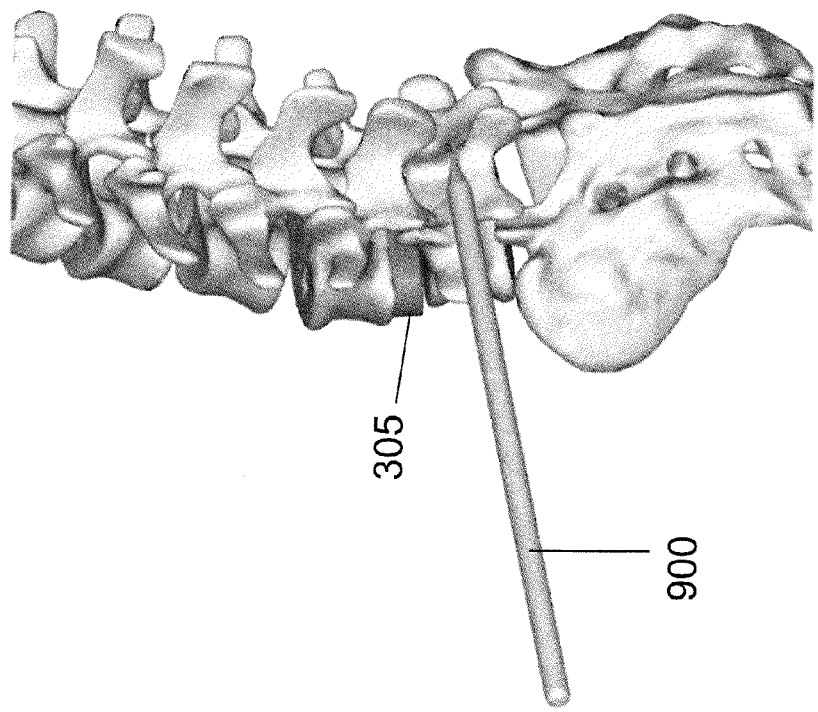
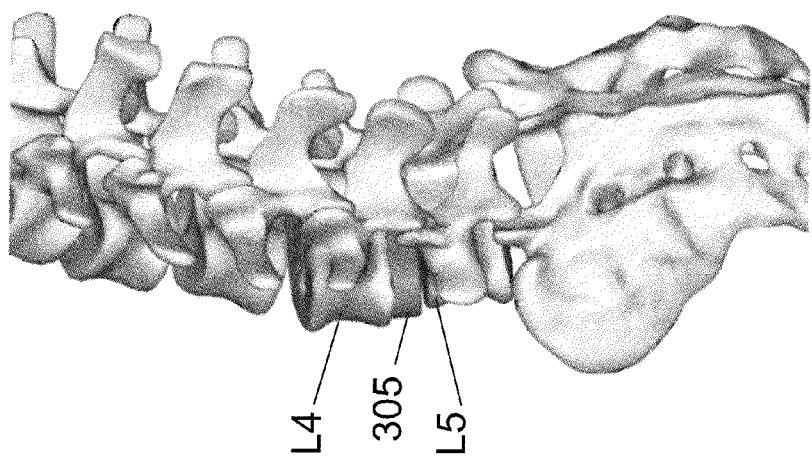

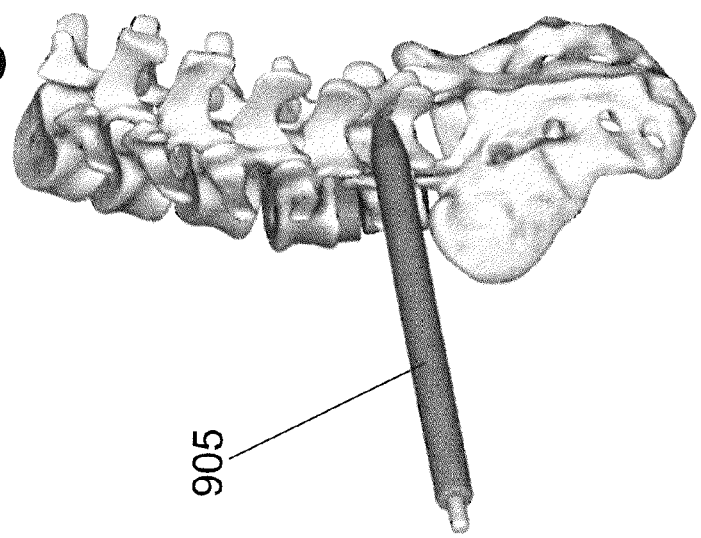
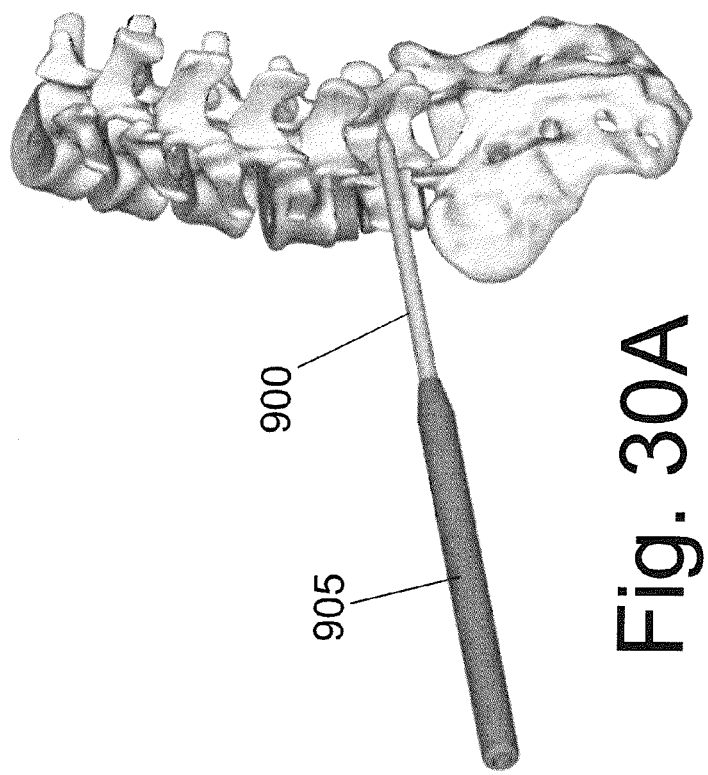

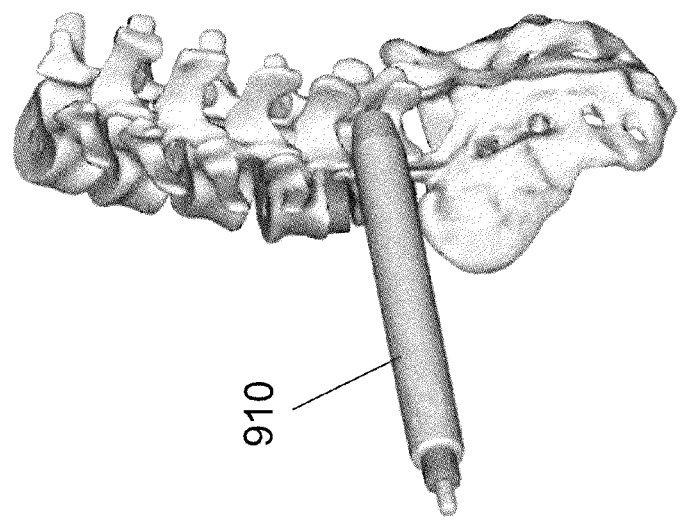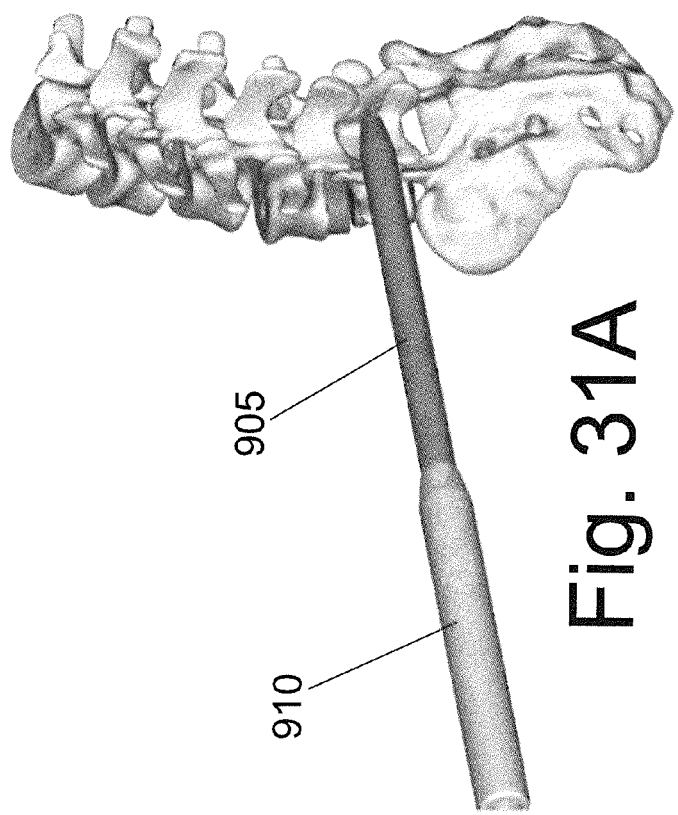

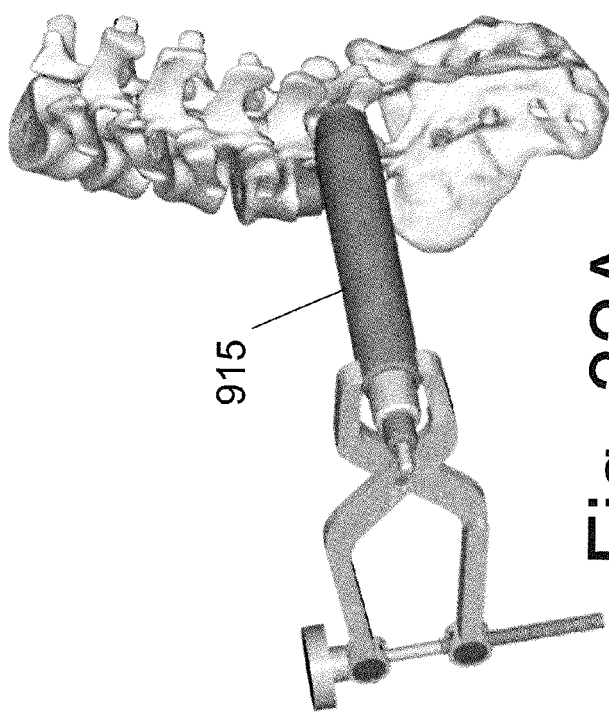
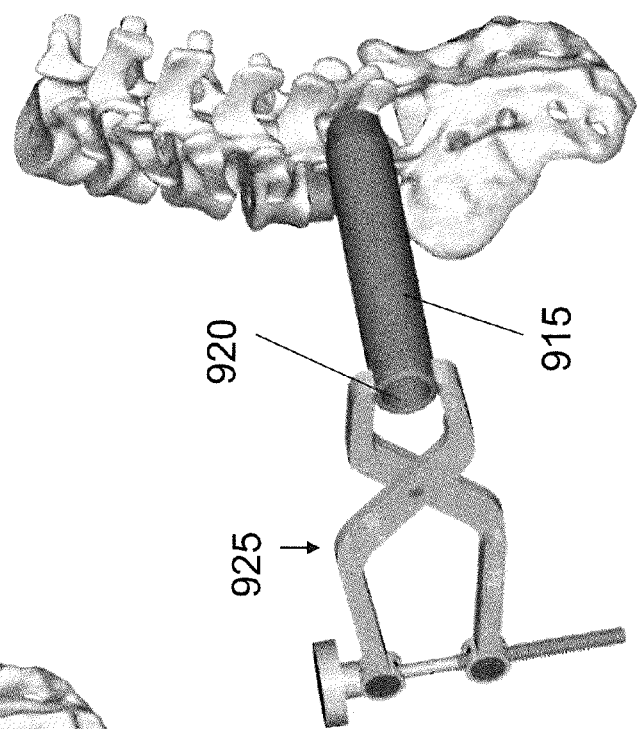
Fig. 32A
Fig. 32B

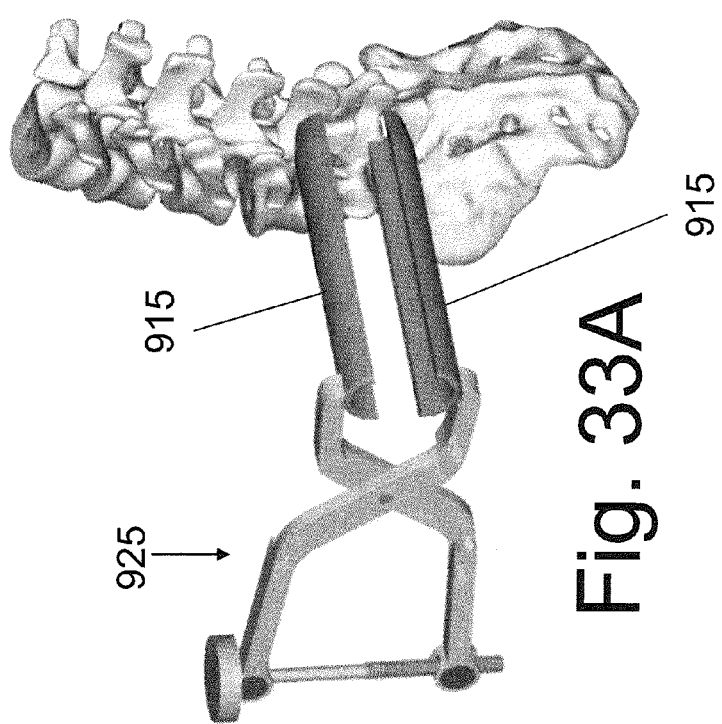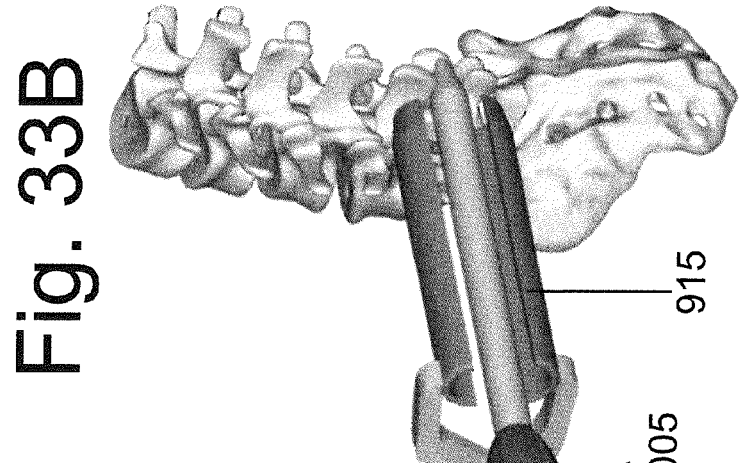

SPINOUS PROCESS FIXATION DEVICES AND METHODS OF USE

REFERENCE TO PRIORITY DOCUMENT

This application claims priority to U.S. Provisional Patent Application Ser. No. 61/461,839, entitled "Spinal Fixation Devices and Methods of Use" by Samy Abdou, filed Jan. 24, 2011. Priority of the provisional filing date is hereby claimed, and the disclosure of the provisional patent application is hereby incorporated by reference in its entirety.

BACKGROUND

This disclosure relates generally to bone fixation systems, components thereof, and methods of implant placement used to adjust, align and maintain the spatial relationship(s) of adjacent bones or bony fragments after surgical reconstruction of skeletal segments. In particular, this disclosure relates to devices that fixate the spinous processes at one vertebral level with the spinous process of another vertebra.

Whether from degenerative disease, traumatic disruption, infection or neoplastic invasion, alteration in the anatomical relationships between the spinal vertebras can cause significant pain, deformity and disability. Spinal disease is a major health problem in the industrialized world and the surgical treatment of spinal pathology is an evolving discipline. The traditional surgical treatment of abnormal vertebral motion is the complete immobilization and bony fusion of the involved spinal segment and an extensive array of surgical techniques and implantable devices have been formulated to accomplish the treatment objective.

Regardless of the specific objectives of surgery, many surgeons employ implantable devices that maintain the desired spatial relationship(s) between adjacent vertebral bodies. The effectiveness of these devices is critically dependant on adequate fixation into the underlying bone. While screw fixation into the pedicle portion of the vertebral body has emerged as a common method of device fixation, it remains a substantial operation with multiple shortcomings.

SUMMARY

There remains a need for the percutaneous delivery of an implant that can rigidly fixate the spinous process of a first superior bone and a second inferior bone of a functional spinal unit. In one embodiment, the device is adapted to forcibly clamp onto the spinous processes of each of the vertebral bones. The implant may be sized to permit sufficient space for the implantation of bone forming material (for bone fusion) within the inter-spinous space adjacent to it. Additionally, or alternatively, the implant may be adapted to contain a bone forming material within an internal cavity, wherein the bone forming material forms a fusion between the first and the second vertebral bones through at least one opening of the internal cavity.

In another aspect of the invention, an orthopedic implant is disclosed. In one embodiment, the implant is configured to be positioned in proximity to a spinous process of a first vertebral bone relative to a spinous process of a second vertebra bone, and the implant includes: an elongated body with a first bone abutment member with a bone abutment surface; a second bone abutment member that couples to a proximal aspect of the elongated body, the second bone abutment member having at least one bone abutment surface; and a locking member adapted to couple to the elongated body, the locking member adapted to forcibly immobilize the spinous process of the first vertebral bone in between the bone abutment surfaces of the first and the second bone abutment members.

In another embodiment, the implant is configured to be at least partially positioned within an interspinous space that is in between the spinous processes of a superior vertebral bone and an inferior vertebra bone.

In another aspect of the invention, a method for the bony fusion of a first target vertebral bone and a second target vertebral bone of a subject is disclosed. In one embodiment, the method comprises: identifying the target vertebral bones on an imaging modality; placing an incision in the lateral skin surface of the subject and developing a lateral surgical corridor to the lateral aspect of a target intervertebral disc space, wherein the target disc space is positioned between the first and the second vertebral bones; positioning an implant within the target intervertebral disc space through the lateral surgical corridor; using an incision in the lateral skin surface of the subject and developing a lateral surgical corridor to the lateral aspect of a target inter-spinous space, wherein the target inter-spinous space is positioned between the spinous processes of the first and the second vertebral bones; and positioning an implant within the target interspinous space.

In another embodiment, the method comprises: identifying the target vertebral bones on an imaging modality; placing a skin incision that is posterior and lateral to the posterior aspect of the pedicles of the target vertebral bones and developing a surgical corridor to a target facet joint, wherein the target facet joint is the ipsilateral facet joint forming an articulation between the first and second target vertebral bones; removing at least a portion of the target facet joint and advancing an implant within a target intervertebral disc space through a trans-foraminal surgical corridor, wherein the target disc space is positioned between the first and the second vertebral bones; developing a surgical corridor to the lateral aspect of a target inter-spinous space, wherein the target inter-spinous space is positioned between the spinous processes of the first and the second vertebral bones; and positioning an implant within the target interspinous space.

The details of one or more embodiments are set forth in the accompanying drawings and description below. Other features, objects, and advantages will be apparent from the following description, the accompanying drawings and from the claims.

BRIEF DESCRIPTION OF THE DRAWINGS

These and other aspects will now be described in detail with reference to the following drawings. In generally, the figures are not necessarily drawn to scale. Also, relative placement of features and elements may be modified for the purpose of illustrative clarity.

FIGS. 3A-3C are various views of a diagrammatic representation of a spinal vertebral bone.

FIGS. 4A-4B are various views of a functional spinal unit that contains two adjacent vertebral bones.

FIG. 5 is a schematic cross-sectional view of a torso at the level of the lumbar spine.

FIG. 8 illustrates perspective views of a segment of the fixation device.

FIG. 9B illustrates various views of another embodiment of the separate member that is shown in FIG. 9A.

FIG. 12 illustrates cross-sectional views of the segment of FIG. 10.

FIGS. 23 and 24 illustrate the device attached to the holding instrument. Note that arms are in the fully withdrawn position and the separate member has been removed.

FIG. 25 illustrates the device attached to the holding instrument. Note that arms are in the fully deployed position and the separate member has been removed.

FIGS. 26A, 26B, 27A, 27B, 28A, and 28B illustrate the procedural steps needed to attach the separate member onto the device of FIG. 23.

FIGS. 29A and 29B area schematic representation of the lumbar spine, wherein an implant has already been positioned within the disc space.

FIGS. 30A and 30B illustrate placement of a larger tissue dilator over the tissue dilators of FIG. 29B.

FIGS. 31A and 31B illustrate placement of a larger tissue dilator over the tissue dilators of FIG. 30B.

FIGS. 32A and 32B illustrate advancement of a distraction device onto the target interspinous space that is to be implanted.

FIGS. 33A and 33B illustrates distraction using the distraction device.

Figure 1:
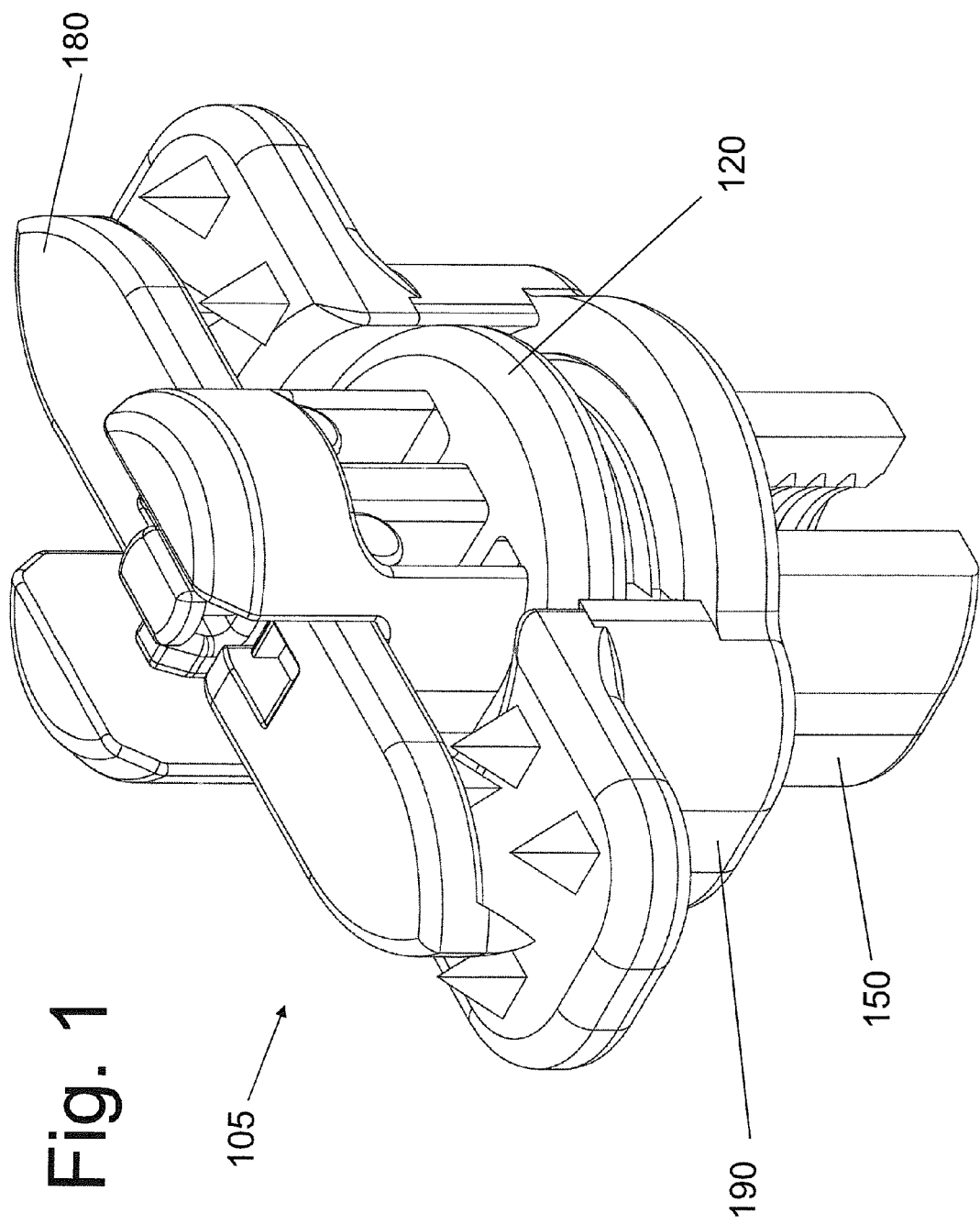
FIG. 1 is a prospective view of a first embodiment of a fixation device.

In order to promote an understanding of the principals of the disclosure, reference is made to the drawings and the embodiments illustrated therein. Nevertheless, it will be understood that the drawings are illustrative and no limitation of the scope of the claims is thereby intended. Any such alterations and further modifications in the illustrated embodiments, and any such further applications of the principles of the disclosed devices as illustrated herein are contemplated as would normally occur to one of ordinary skill in the art.

DETAILED DESCRIPTION

Described herein are devices and methods for the treatment of abnormal spinal stability and stenosis of the spinal canal by the implantation of orthopedic devices between skeletal segments. In an embodiment of the invention, a device is disclosed that rigidly fixates the spinous processes of two adjacent vertebral bones relative to one another. In one embodiment of device use, the implant is percutaneously placed into the interspinous space and may be used to provide decompression of spinal stenosis by retaining the spinous process in the distracted position. The implant also affixes the spinous processes of the vertebral bones on either side of the implanted inter-spinous space in order to retain and immobilize the vertebral bones relative to one another.

The device is inserted from a skin incision that is on a first side of the interspinous space between a first and a second spinous process. Rotatable members of the implant are advanced across the interspinous space from the first side (ipsilateral to site of skin incision) to a second contralateral side. Preferably, the long axis of the implant is positioned substantially parallel to the trajectory used for implantation. After at least a segment of the rotatable members are positioned on the contralateral side of the interspinous space, a mechanism is engaged in order to produce movement of at least one rotatable member, wherein, after rotation, the rotated rotatable members is positioned with at least a segment overlying a segment of the lateral surface of the first or the second spinous process.

A separate member is then positioned on the side of the spinous process that is ipsilateral to the site of skin incision. A locking member is used to retain the separate member attached to the device. As the locking member is advanced further, the spinous processes are forcibly captured between the rotatable members on the contralateral side of the spinous processes and the separate member positioned on the ipsilateral side of the spinous processes.

In a another embodiment, the mechanisms for rotation of the rotatable arms as well as the locking mechanism are engaged and actuated through deployment instruments that are substantially positioned parallel to the trajectory of device implantation. Further, the engagable segments of these mechanisms are located on the ipsilateral side of the spinous processes at the time of engagement by the deployment instrument (whereas the rotatable members are located on the contralateral side of the spinous processes).

In an embodiment of implant use, the implant is advanced into the posterior column (into the interspinous space) of a spinal segment while another orthopedic implant is placed into the anterior column of the same spinal segment using a lateral approach to the anterior column (these operations are known as extreme lateral interbody fusion (XLIF), direct lateral interbody fusion (DLIF), and the like). In this method both implants may be placed through a single lateral skin incision or two adjacent skin incisions to provide a truly percutaneous or minimally invasive approach. Further, this method provides circumferential (i.e., anterior and posterior) expansion and decompression of the spinal canal so as to treat spinal stenosis though anterior and posterior decompression of the spinal canal. That is, placement of an anterior column implant (via XLIF, DLIF and the like) provides anterior decompression of the spinal column, whereas placement of the disclosed implant into the posterior column (preferably between the spinous processes) provides posterior decompression of the spinal column—and both may be performed through a common flank approach (see FIG. 5). In another embodiment of use, the device may be deployed through a single incision that is posterior and lateral to the posterior aspect pedicle of the spinal levels to be implanted (see FIG. 7). (A surgical procedure that employs a similar incision is known to those of ordinary skill in the art as transforaminal lumbar interbody fusion (TLIF) or posterior lumbar interbody fusion (PLIF).) Bone screws are advanced into the pedicle portion of bone on the side of the vertebrae that is ipsilateral to the incision. The screws are rigidly interconnected with a rod. The device disclosed herein is then placed through the same skin incision into the inter-spinous space. While contralateral pedicle screws may be also placed by the operating surgeon, the implanted interspinous device obviates the need for contralateral screw placement.

Figure 2:
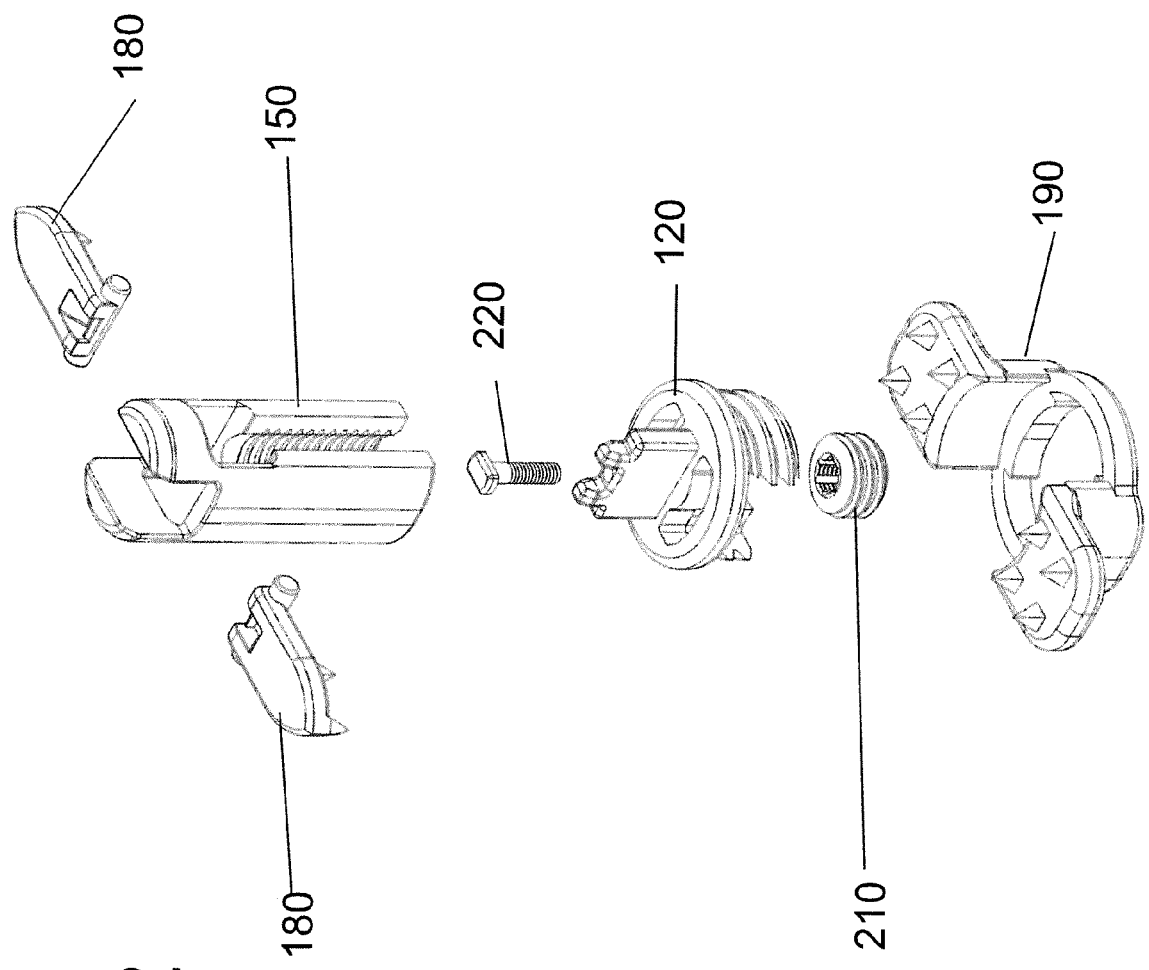
FIG. 2 is an exploded view of the device of FIG. 1.

FIG. 1 is a perspective view of an embodiment of a fixation device 105 in an assembled state. FIG. 2 depicts a perspective view of the device 105 in an exploded view. The fixation device 105 includes a plate member 120, rotation arm 180, and an advancing deployment member 150, each of which will be described in more detail below. The fixation device 105 also includes a nut 210 and a screw 220 (shown in FIG. 2) and these members play a role in rotation of the rotatable arms. Separate member 190 functions to abut the ipsilateral side of the spinous processes and is shown in FIG. 9.

The device 105 may be used to interconnect, fixate and compress the spinous process at one vertebral level with the spinous process of another adjacent vertebral level. The devices permits a surgeon to percutaneously implant the device into the posterior column of the spine from a lateral, or flank incision, as will be discussed in more detail below.

As used herein, the anterior column generally designates a portion of the vertebral body and/or Functional Spinal Unit (FSU) that is situated anterior to the posterior longitudinal ligament. Thus, its use in this application encompasses both the anterior and middle column as discussed in Denis (see "The three column spine and its significance in the classification of acute thoracolumbar spinal injuries." Denis, F. Spine 1983 November-December; 8(8):817 31, which is incorporated by reference in its entirety.) The illustrations and definitions of anatomical structures are known to those of ordinary skill in the art, They are described in more detail in Atlas of Human Anatomy, by Frank Netter, third edition, Icon Learning Systems, Teterboro, N.J. The text is hereby incorporated by reference in its entirety. It should be appreciated that the directional language and terms regarding orientation such as upper, lower, upward, downward etc. are used merely for convenience of description and are not intended to be limiting.

FIGS. 3A-3C are diagrammatic representations of a spinal vertebral bone 802 in multiple views. For clarity of illustration, the vertebral bone of FIGS. 3A-3C and those of other illustrations disclosed herein are represented schematically and it should be appreciated that actual vertebral bodies may include anatomical details that are not shown in these figures. Further, it is understood that the vertebral bones at a given level of the spinal column of a human or animal subject will contain anatomical features that may not be present at other levels of the same spinal column. The illustrated vertebral bones are intended to generically represent vertebral bones at any spinal level without limitation. The disclosed devices and methods may be applied at any spinal level.

Vertebral bone 802 contains an anteriorly-placed vertebral body 804, a centrally placed spinal canal 806 and posteriorly-placed lamina 808. The pedicle segments 810 of vertebral bone 802 form the lateral aspect of the spinal canal 806 and connect the laminas 808 to the vertebral body 804. The spinal canal 806 contains neural structures such as the spinal cord and/or nerves. A midline protrusion termed the spinous process (SP) extends posteriorly from the medial aspect of laminas 808. A protrusion extends laterally from each side of the posterior aspect of the vertebral bone 802 and is termed the transverse process (TP). A right transverse process (RTP) extends to the right and a left transverse process (LTP) extends to the left. A superior protrusion extends superiorly above the lamina 808 on each side of the vertebral midline and is termed the superior articulating process (SAP). An inferior protrusion extends inferiorly below the lamina 808 on each side of the vertebral midline and is termed the inferior articulating process (IAP). Note that the posterior aspect of the pedicle 810 may be accessed at an indentation 811 in the vertebral bone 802 between the lateral aspect of the SAP and the medial aspect of the transverse process (TP). In surgery, it can be common practice to anchor a bone fastener into the pedicle portion 810 of a vertebral bone 802 by inserting the fastener through indentation 811 and into the underlying pedicle 810.

FIGS. 4A and 4B illustrate a FSU, which includes two adjacent vertebrae and the intervertebral disc between them. The intervertebral disc resides between the inferior surface of the upper vertebral body and the superior surface of the lower vertebral body, although it is not specifically shown in the figures. FIG. 4A illustrates the posterior surface of the adjacent vertebrae and the articulations between them. FIG. 4B illustrates an oblique view. The FSU contains a three joint complex between the two vertebral bones, with the intervertebral disc comprising the anterior joint. The posterior joints include a facet joint 814 on each side of the midline, wherein the facet joint 814 contains the articulation between the TAP of the superior vertebral bone and the SAP of the inferior bone.

The interspinous space is generally defined as the space immediately between the spinous processes of a superior vertebral bone and the spinous process of an immediately adjacent inferior vertebral bone. The interspinous space is limited anteriorly by the spinal canal 806 and posteriorly by the posterior tip of the spinous processes. For the purpose of this application, the right lateral aspect of the interspinous space is limited by the right lateral side of the spinous processes whereas the left lateral aspect of the interspinous space is limited by the left lateral side of the spinous processes. Note that the spinous processes of adjacent vertebral bones may be rotated in the axial plane relative to one another because of biological and/or individual variation (schematically shown in FIG. 4A). The interspinous space would continue to be defined as residing between the spinous processes of the superior and inferior vertebral bones.

Now with respect to FIG. 8, the plate member 120 of the fixation device 105 includes a generally circular platform having a central protrusion 124. The central protrusion 124 of the plate member 120 includes a shoulder 1246 and an upward protrusion 1248 on either side of a depression 1242. Full thickness holes 132 are positioned on each side of protrusion 124 and have a shape complementary to and adapted to accept member 150 therethrough, as will be described in more detail below. A central opening 1242 is positioned within notch 1241 and has a shape configured to accept screw 220. Unlike holes 132, central opening 1242 need not extend fully through the plate member. Plate member 120 has a coupling element 136 on the second surface 123 opposite the central protrusion 124. The coupling element 136 includes a pair of opposing projections each of which has a threaded outer surface 1360 and a notched inner surface 1364 (see FIG. 8). The coupling element 136 is used to couple the fixation device 105 to a deployment instrument for insertion and implantation, as will be described in more detail below.

Figure 9A:
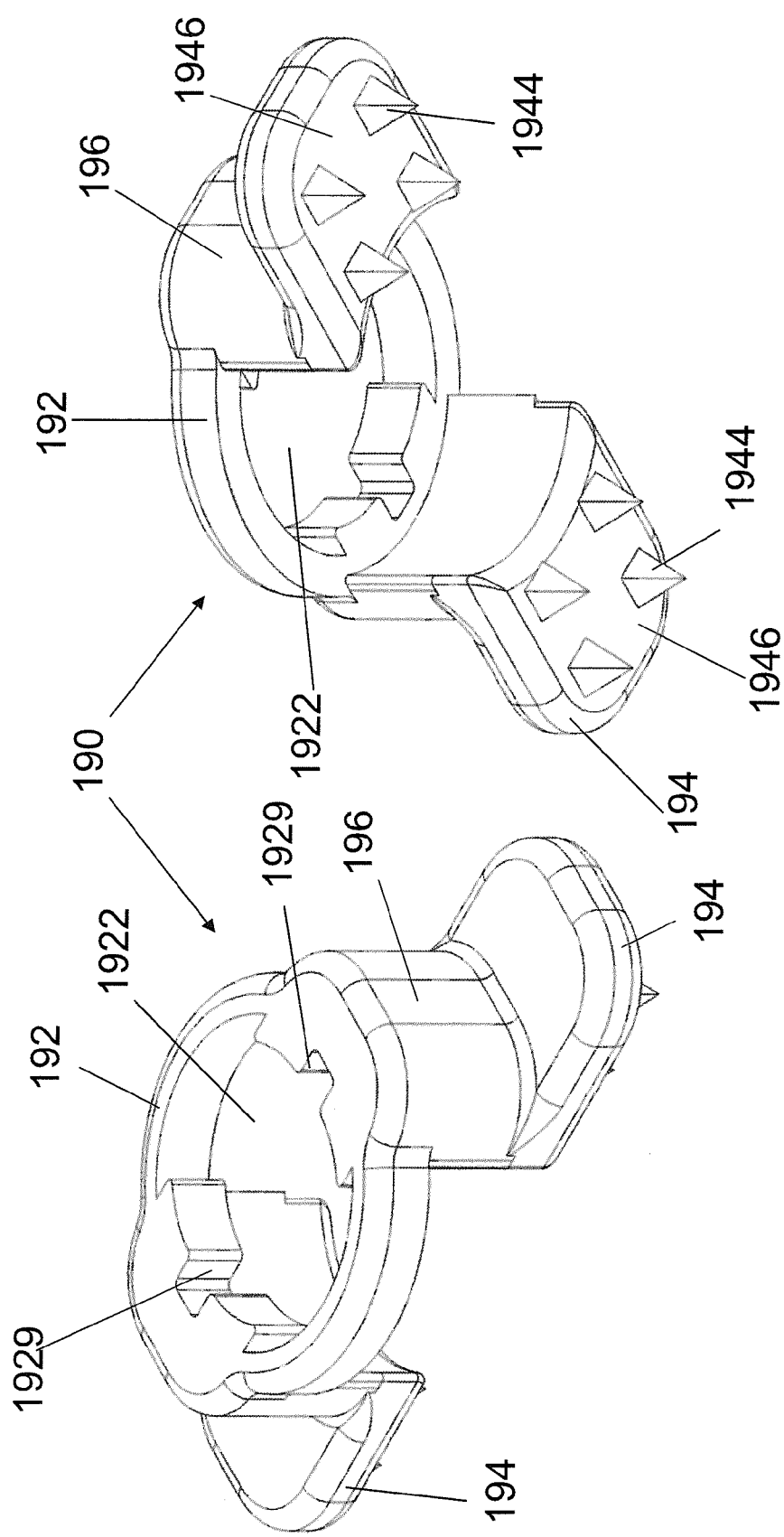
FIG. 9A illustrates perspective views of another segment of the fixation device.

Separate member 190 is shown in FIGS. 9A and 9B. Member 190 has central member 192 having a substantially circular configuration. An internal bore 1922 is positioned within member 192 and the bore is adapted to accept, among other structures, the protruding elements 162 of member 150—as discussed below. Foot member 194 contains an abutment surface 1946 and at least one protrusion 1944. Each protrusion 1944 is adapted to penetrate the bony surface of the spinous process and comprises a sharpened tip. Member 194 is attached to member 192 by side member 196. The abutment surface 1946 of foot member 194 is adapted to abut a side wall of the spinous process, wherein the plane of the abutment surface is offset from the plane of member 192 as shown in FIG. 9A. In this way, member 192 is positioned off of the side of a spinous process when abutment surface 1946 is positioned in contact with the side of the spinous process. Member 190 may contain at least one notch 1929 that is adapted to receive a process of insertion instrument 715 (see discussion below).

In addition, member 194 may be configured to rotate relative to side member 196 (FIG. 9B). In this way, the separate member 190 may have a smaller size during implantation and require less soft tissue retraction during placement. After member 190 is positioned in proximity to the target interspinous space, member 194 may be rotated to a deployed position wherein member 194 is substantially parallel to the sides of the spinous processes to be fixated. FIG. 9B illustrates an example of a separate member 190 with at least one rotatable member 194 that is joined to member 196 by pin 201. It is understood that while the abutment surface is adapted to rotate relative to the side member along direction R, it is equally possible to have each member 194 rotate in the opposite direction relative to member 196. Note that the implantation procedure will be illustrated using the rigid embodiment of FIG. 9A. However, it is understood that implantation procedure may be alternatively performed with a separate member having a rotatable member 194.

Figure 10:
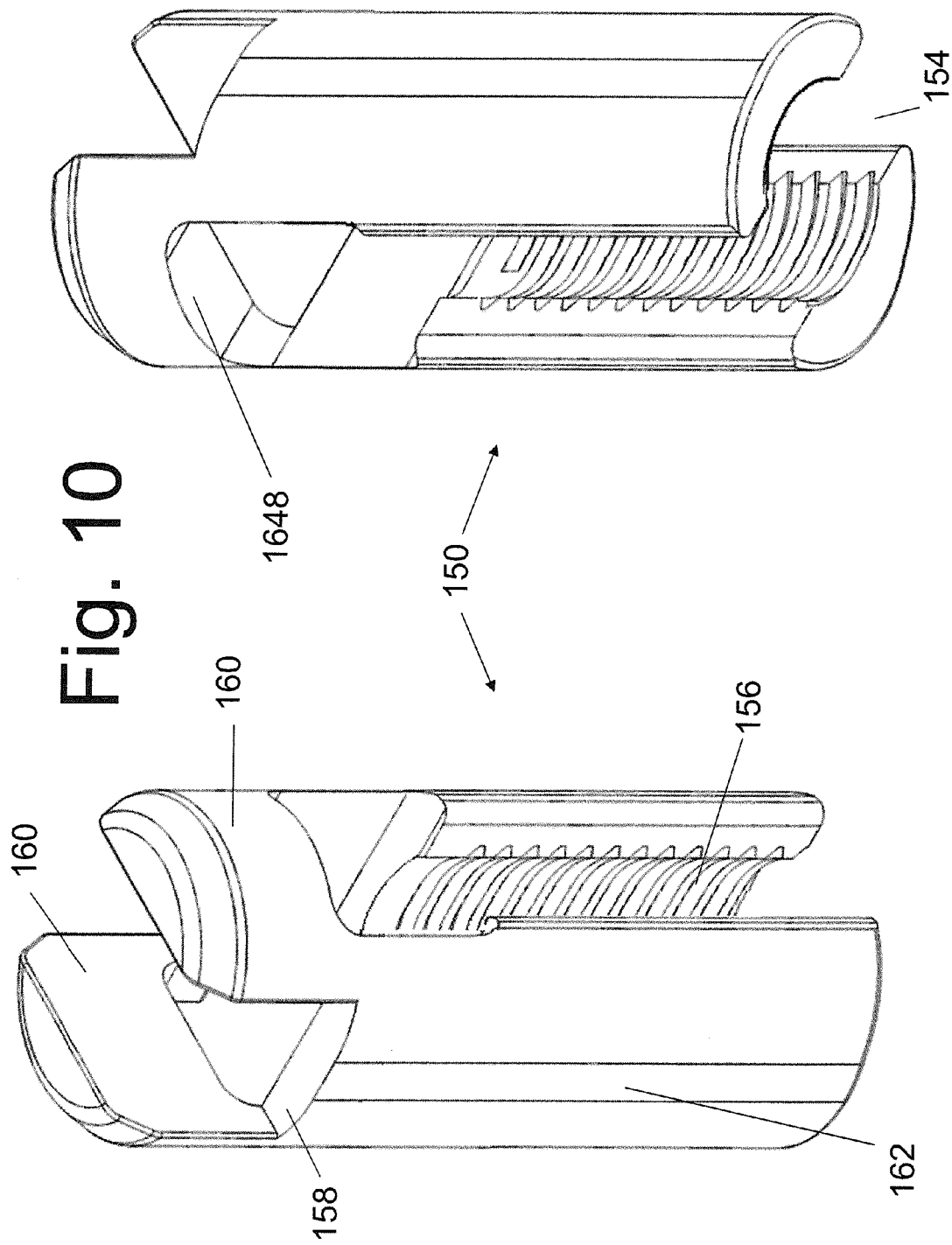
FIG. 10 illustrates perspective views of another segment of the fixation device.
Figure 11:
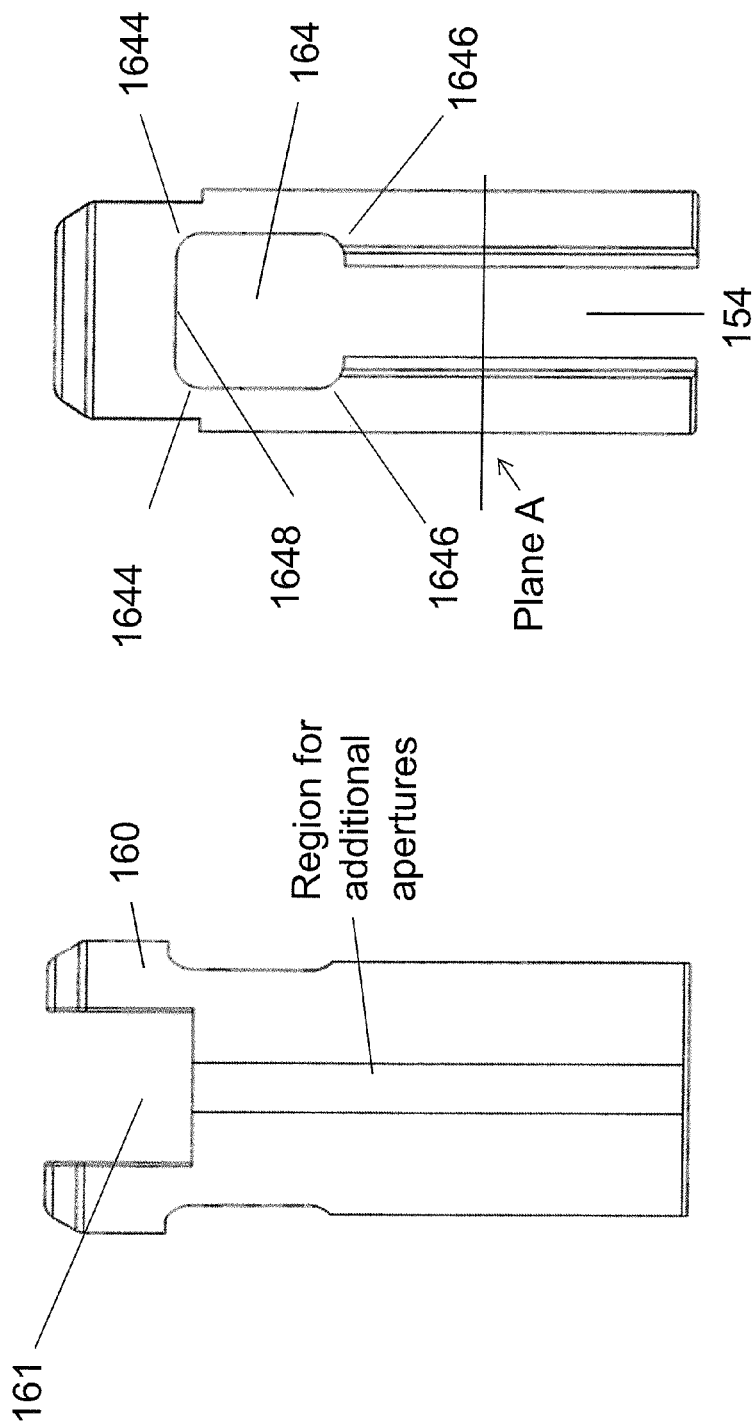
FIG. 11 illustrates orthogonal views of the segment of FIG. 10.

FIGS. 10-12 depict perspective views of an advancing deployment member 150. Member 150 is a generally cylindrical element having a central bore 154 extending from a first region to a second region. The first region of the member 150 through which central bore 154 extends has opposing, downward-extending elements 162. The second region of the member 150 has opposing, upward-extending elements 160. The cross-section of the opposing, downward-extending elements 162 is complementary to holes 132 in the plate member 120 such that the downward-extending elements 162 may be drawn through the holes 132. The downward-extending elements 162 are shown as being generally cylindrical on their outer surface although it should be appreciated that the geometry of these elements 162 (and the complimentary geometry of the holes 132 in the plate member 120) can vary. The inner surface of elements 162 facing the central bore 154 may have threads 156. The bore 154 has an expanded region that forms a window 164, wherein a window 164 has upper surfaces 1644 and shoulders 1646. The segment of the ledge that connects each corner 1644 is an abutment surface 1648. Surface 1648 is abutted by shoulder 1246 when rotation arms 180 are fully deployed—as will be described below.

Opposing, upward-extending elements 160 are shown as being partially cylindrical on their outer surface although it should be appreciated that the geometry of these elements can vary. Upward-extending elements 160 have an inner surface facing the bore 154. The elements 160 create a second channel 161 through member 150 that intersects the upper region of bore 154. Channel 161 has a generally U-shaped geometry formed by the inner surfaces of opposing elements 160 and surface 158. The channel 161 in the upper region of member 150 is off-set by approximately 90 degrees from window 164. It should be appreciated that the angle of off-set can vary. Opposing, downward-extending elements 162 are drawn through holes 132 such that the elements 162 interdigitate with the coupling element 136 at the inferior surface of the plate member 120. The outer threaded surface of the coupling element 136 is available for engagement by the deployment instrument as will be described in more detail below. The inner threads 156 of the elements 162 are also available for engagement by the locking nut 210, as will also be described below.

In another embodiment, the outer surface of member 162 may contain at least one additional full thickness bore hole that is adapted to extend from the outer surface to the internal cavity of bore 154 (for example, along plane A of FIG. 11). While the at least one bore hole may be positioned on one downward-extending element 162 alone, at least one hole is placed on each of the two downward-extending elements 162 in another embodiment. In use, at least a portion of the internal cavity (of bore 154) would be packed with bone forming material so that a bony fusion can develop between the two spinous processes that abut the implant (i.e., the spinous processes of the upper and the lower vertebral bones that are attached to the implant). The bony fusion would extend from one spinous process, across the bore hole(s) of one of the downward-extending elements 162, across a segment of bone forming material of bore 154, across the bore hole(s) of the opposing downward-extending elements 162 and onto the other spinous process.

Figure 13:
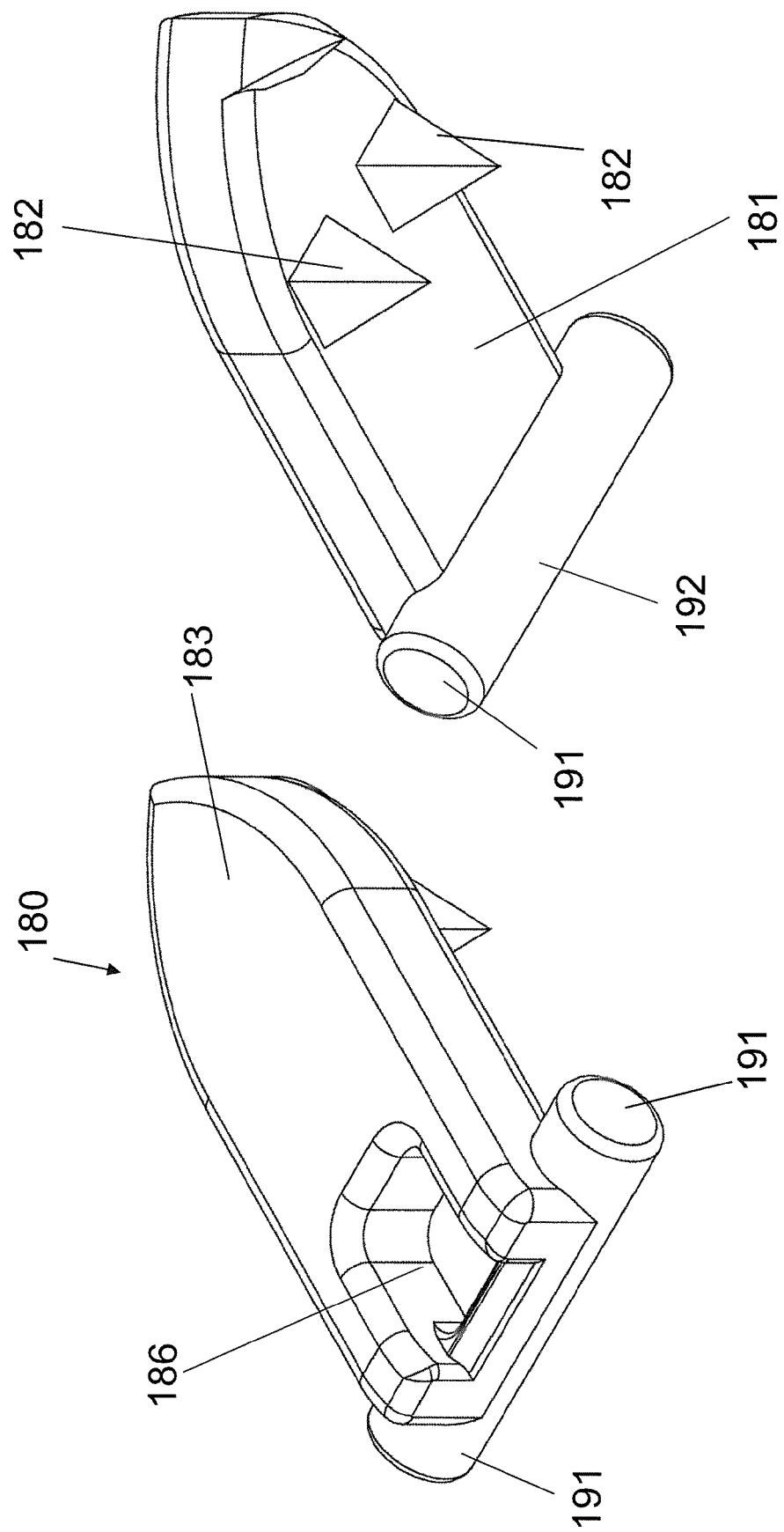
FIG. 13 illustrates perspective views of another segment of the fixation device.
Figure 14:
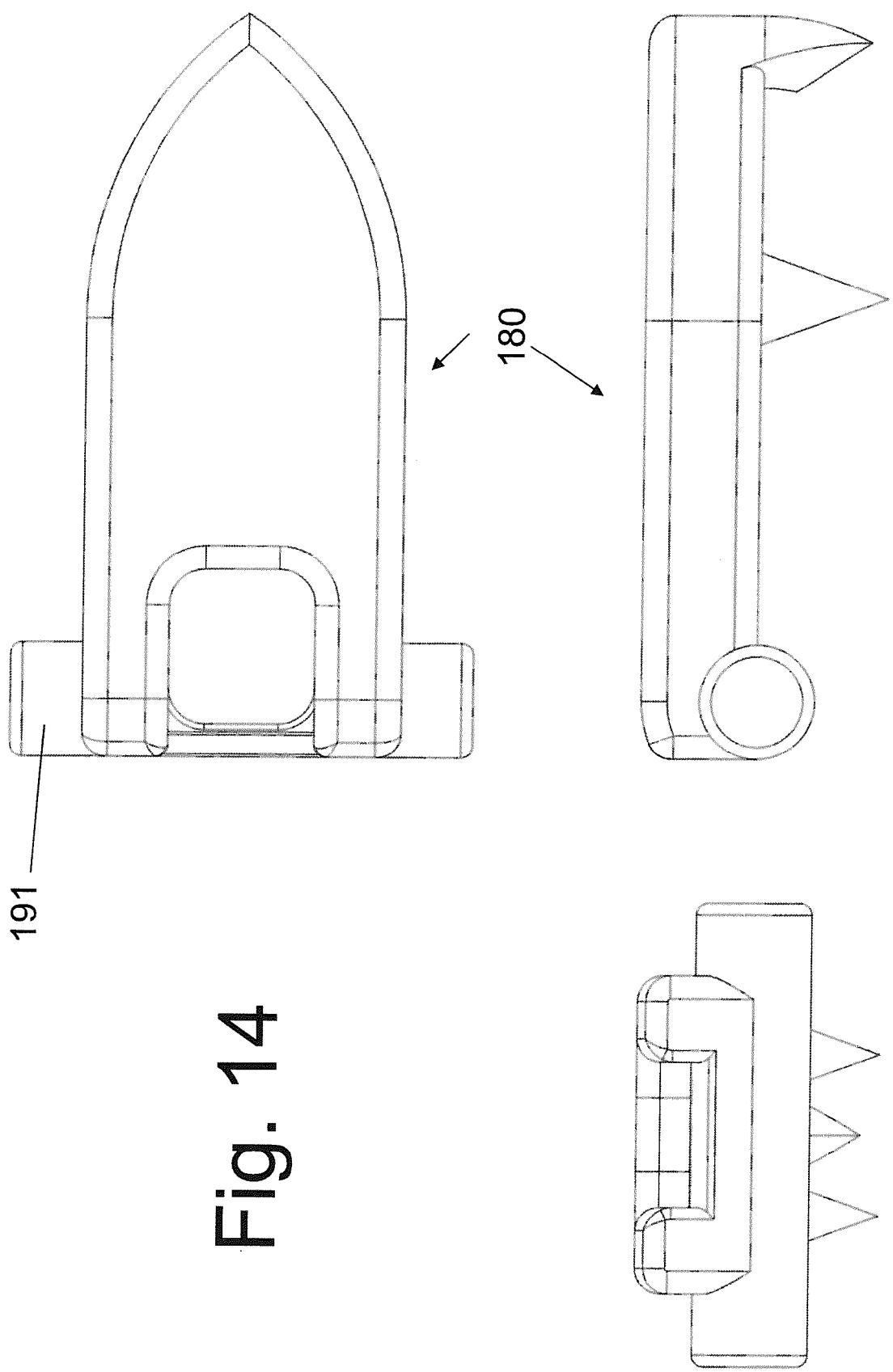
FIG. 14 illustrates orthogonal views of the segment of FIG. 13.
Figure 15:
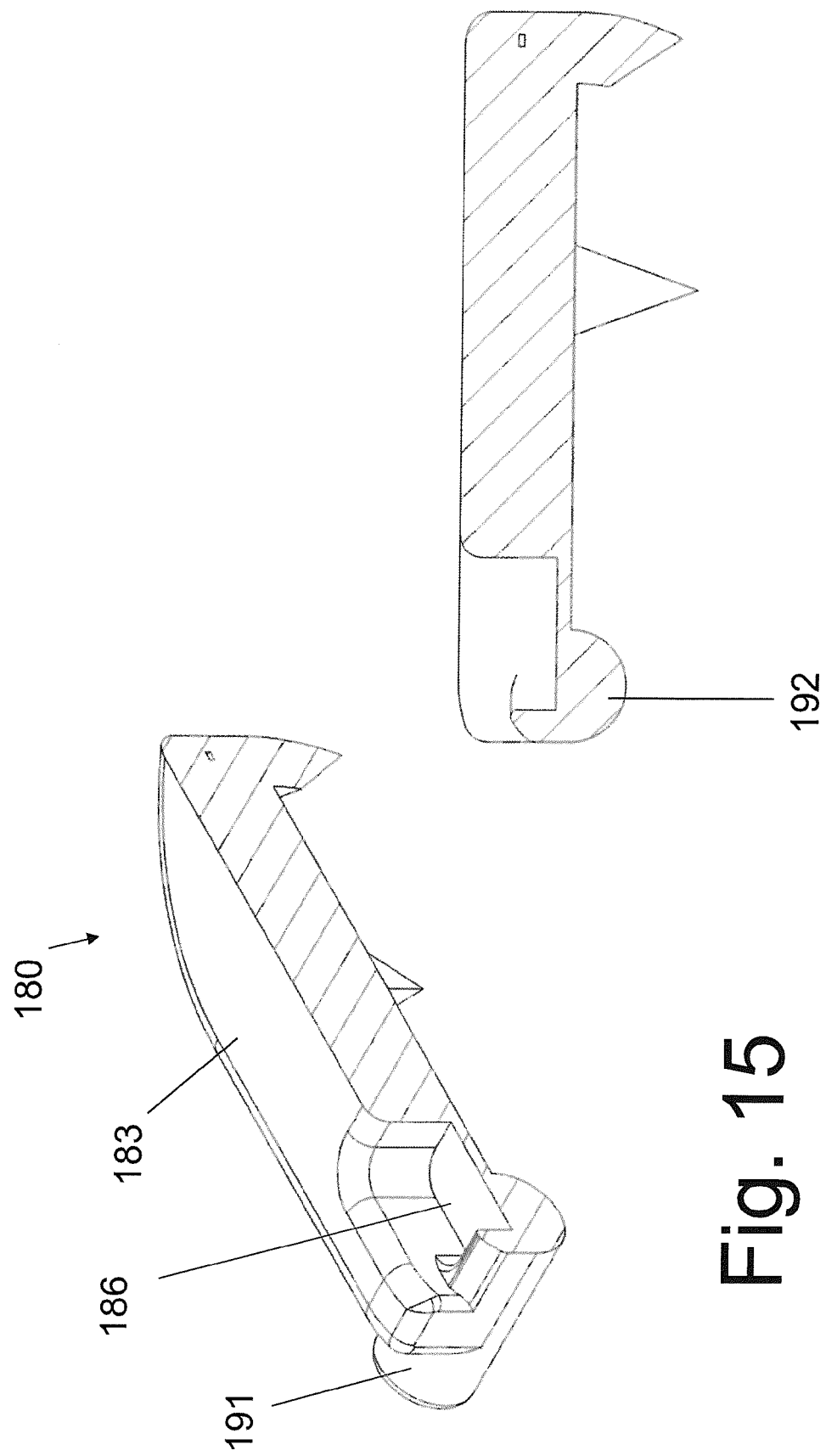
FIG. 15 illustrates cross-sectional views of the segment of FIG. 13.

FIGS. 13-15 depict perspective views of a rotation arm 180. Although the FIGS. 13-15 illustrate a single rotation arm 180, it should be appreciated that the fixation device 105 may include two rotation arms 180 positioned in adjacent relationship to one another. It should also be appreciated that the paired rotation arms 180 may be coupled together to form an integrated, articulating element or they may comprise separate components as shown in the figures. (An integrated articulating element may include, for example, a single bar having two rigidly attached arms 180.)

Rotation arms 180 have a generally flat, elongate extension region 185 extending outward from a central, cylindrical hinge element 192. The elongate extension region of the rotation arms 180 are sized and configured to be contained within member 150 between opposing, upward-extending elements 160 inside bore 154. An end region 191 of each hinge element 192 extends at least partially through a portion of window 164. As such, the rotation arms 180 are configured to translate upward and downward through the bore and between upward-extending elements 160. This upward and downward translation through the bore 154 is limited by the end region 191 of each hinge element 192 extending through the window and abutting shoulder 1646 at a lower end of the window 164 and surfaces 1644 at an upper end of the window 164.

Rotation arms 180 have an upper surface 183 having an indentation 186 positioned near the central hinge element 192. When the rotation arms 180 are positioned within the bore 154 of member 150, they are approximately perpendicular to the plane of the plate member 120. The hinge elements 192 are adjacent to one another and the end region 191 of each hinge element 192 extends at least partially through a portion of window 164. The upper surface 183 of each rotation arm 180 is in contact with one another or at least in close proximity to each other such that the indentations 186 on the upper surface 183 align with one another forming a pocket 187. The pocket 187 is configured to contain the head of screw 220 (see for example FIG. 18).

The rotation arms 180 are configured to rotate or articulate around the axis of the hinge member 192 and relative to the plane of the plate member 120. Each extension region 185 rotates away from one another and insert down through U-shaped channel 161 until the arms 180 approach a generally parallel position relative to the plate member 120. Rotation arms 180 have a bone-engaging surface 181 comprising one or more elements 182 extending therefrom. Elements 182 may have a sharpened tip so that they penetrate the surface of the spinous processes, grip bone and aid in anchoring and compression of the arms 180 onto the vertebral bone.

Figure 16:
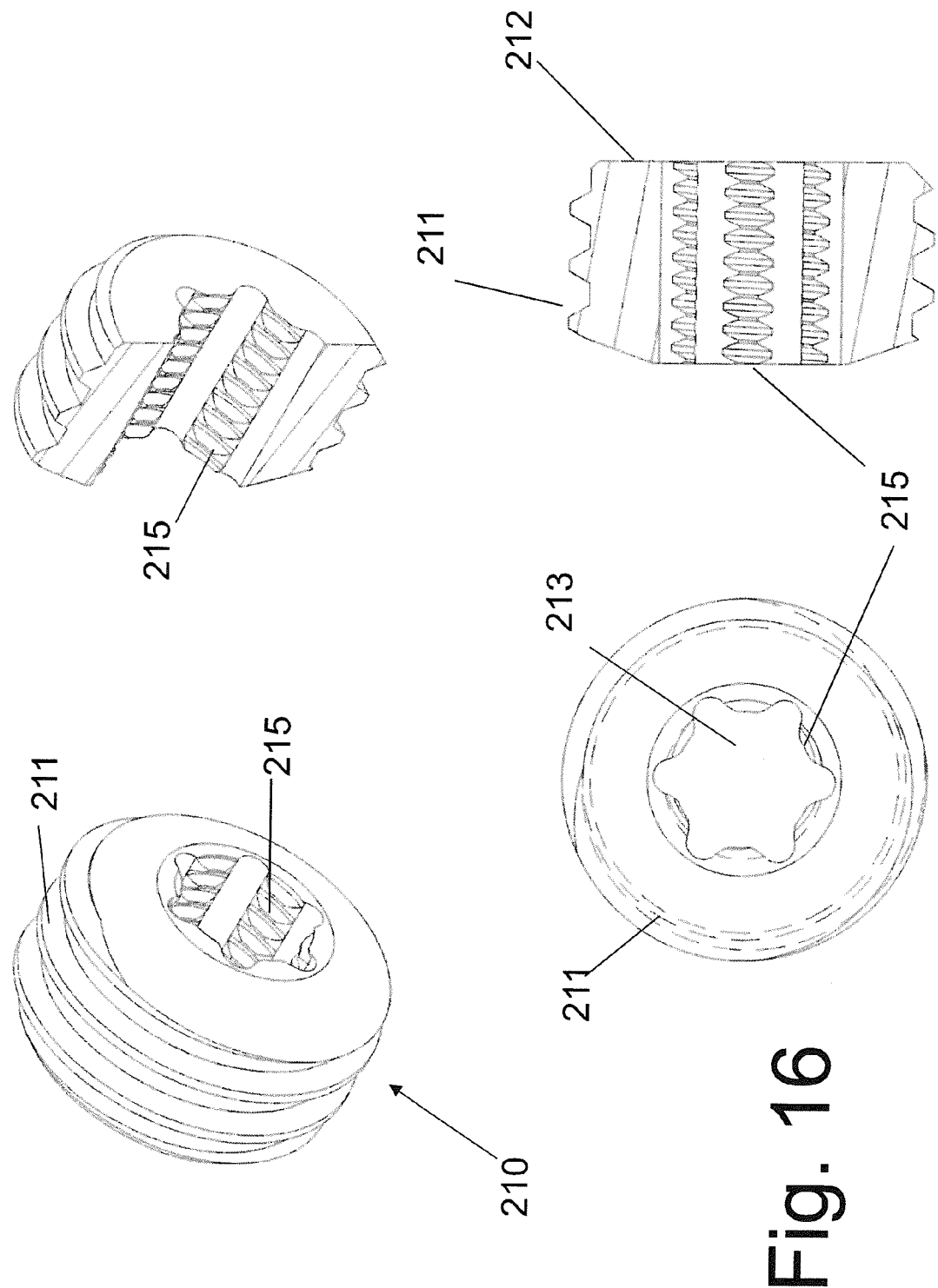
FIG. 16 illustrates a locking nut.

Locking nut 210 is shown in FIG. 16. Locking nut comprises threads 211 on an outer surface and an opening 213. In an embodiment, the opening 213 is engaged with a driving tool having a complimentary shape. While illustrated as a "torx" drive, it should be appreciated that other configurations besides this shape are considered herein. In the assembled state of fixation device 105, the nut 210 threadedly engages the inner threads 156 on opposing, downward-extending elements 162 of member 150. Nut 210 may have a flattened upper surface 212 configured to contact a portion of the plate member 120 positioned between holes 132 and below central protrusion 124. As the nut 210 is rotated it engages and draws downward the elements 162 of member 150. This threading action results in the elements 162 being drawn downward through holes 132 and the upward translation of rotation arms 180 through bore 154. In an embodiment, opening 213 further contains threads 215.

The fixation device 105 described herein acts to space apart the spinous processes and prevent these from bottoming out against one another. The fixation device described herein also fixates the spinous processes relative to one another by compressing them between the plate member and the rotation arms. In this way, the fixation device 105 is also configured to prevent movement of the spinous processes towards each other (as occurs with vertebral extension) and away from each other (as occurs with vertebral flexion).

Figure 17:
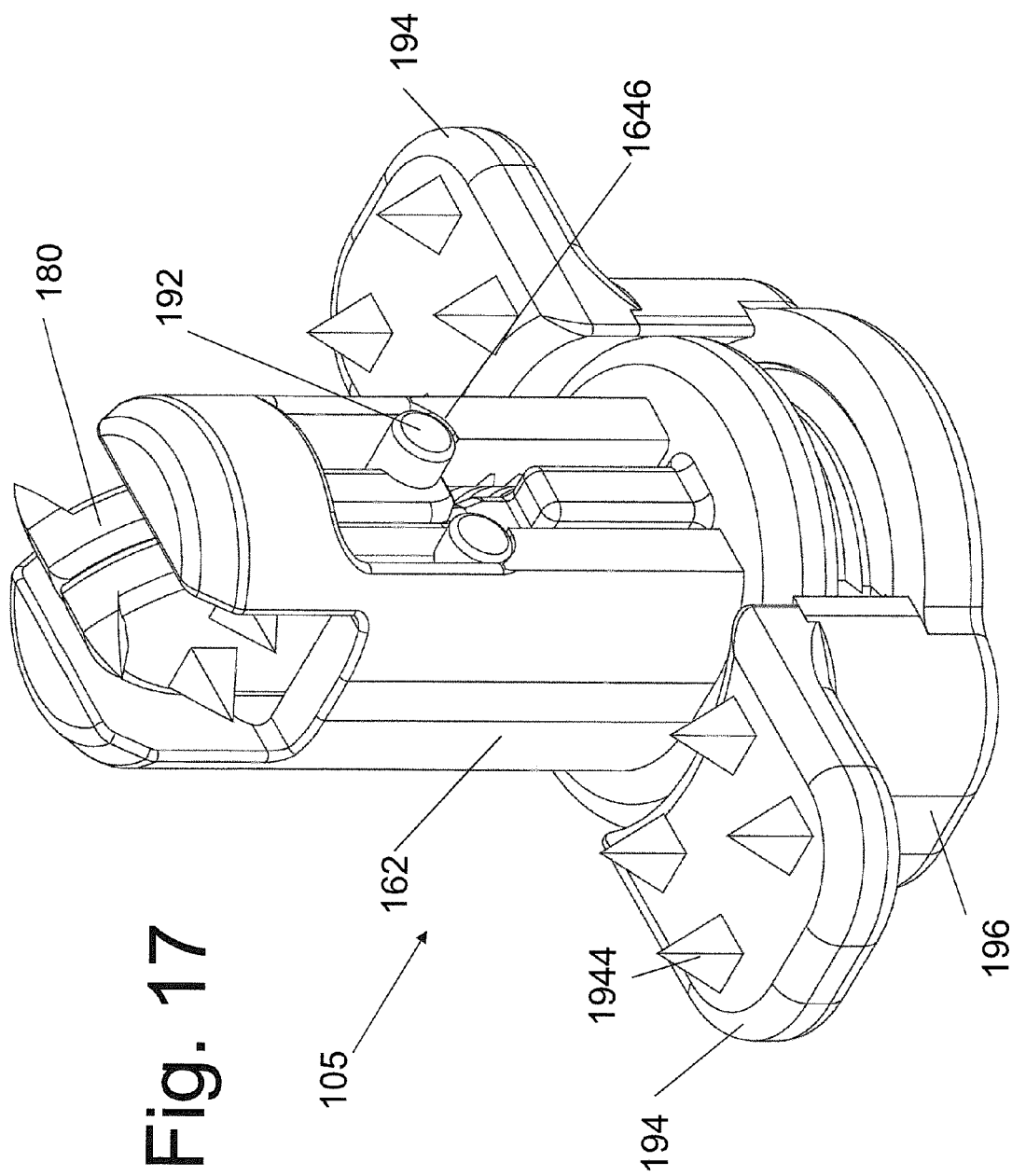
FIG. 17 is a perspective view of the assembled fixation device with the arms in the withdrawn position.
Figure 18:
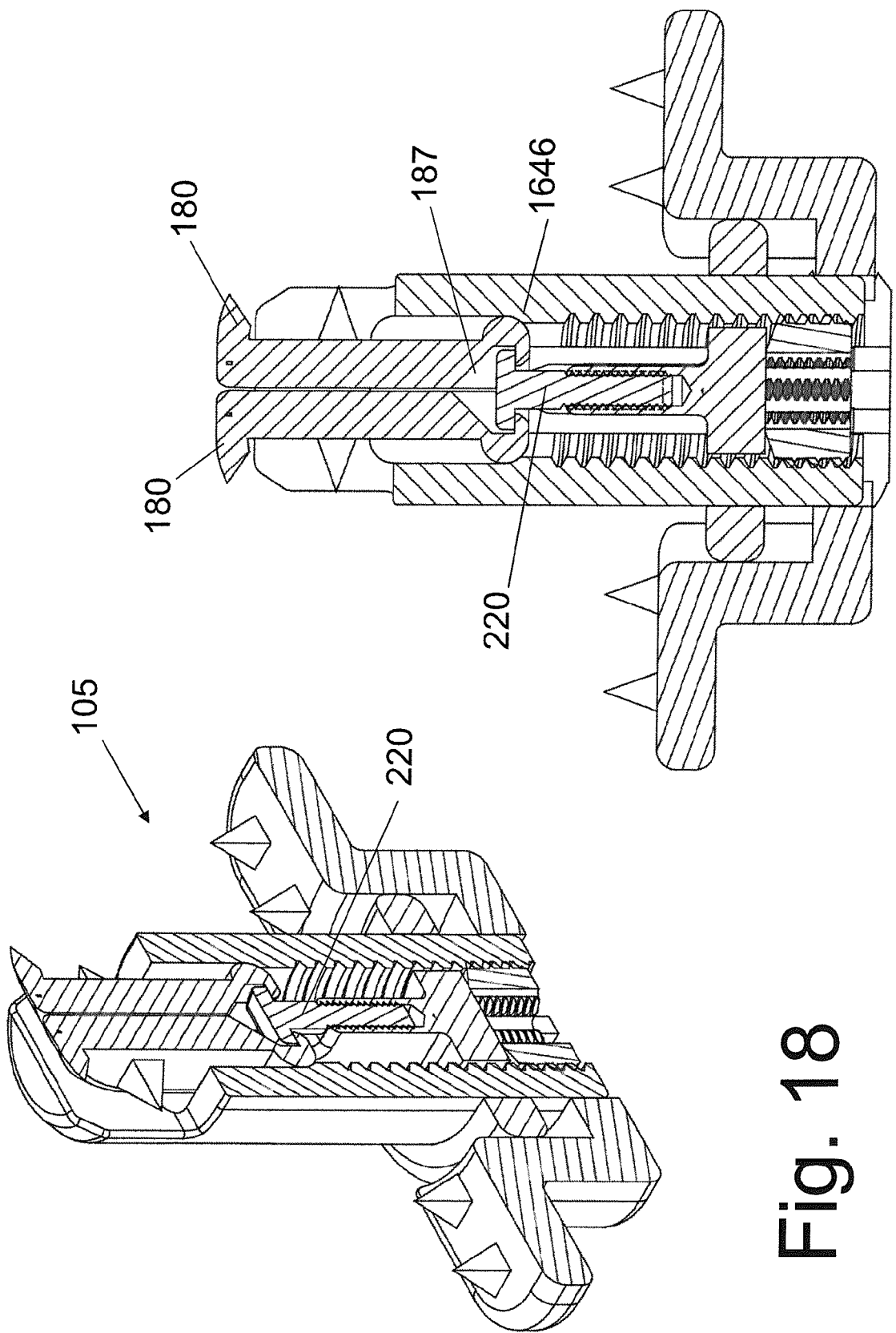
FIG. 18 illustrates cross-sectional views of the device of FIG. 17.

The rotation arms are configured to reversibly transition from the fully withdrawn to the fully deployed state by rotation of threaded locking nut 210. FIGS. 17 and 18 illustrate perspective and cross-sectional views of the fixation device 105 with rotation arms 180 in the fully withdrawn state. Rotation arms 180 are largely contained within member 150 such that the distal aspect of arms 180 extend into the upper region of member 150 between elements 160 and the hinge 192 is positioned within window 164. Screw 220 extends through hole 1242 in central protrusion 124 such that the flanged region or the head of screw 220 is positioned within the pocket 187. The pocket 187 is formed by the alignment of the indentations 186 on the upper surface of rotation arms 180 when in a state flush with one another. At least a portion of the end region 191 of each side of hinge 192 extends through window 164. When the rotation arms 180 are in their downward-most fully withdrawn position, end region 191 of the hinge element 192 abuts shoulders 1646 (see FIGS. 17 & 18). As locking nut 210 is rotated, downward-extending elements 162 of member 150 are drawn through holes 132 of plate member 120. The hinge elements 192 are translated upward through bore of member 150 until end region 191 of the hinge elements 192 abuts surface 1644 (see FIGS. 21 and 22) as will be described in more detail below.

Figure 19:
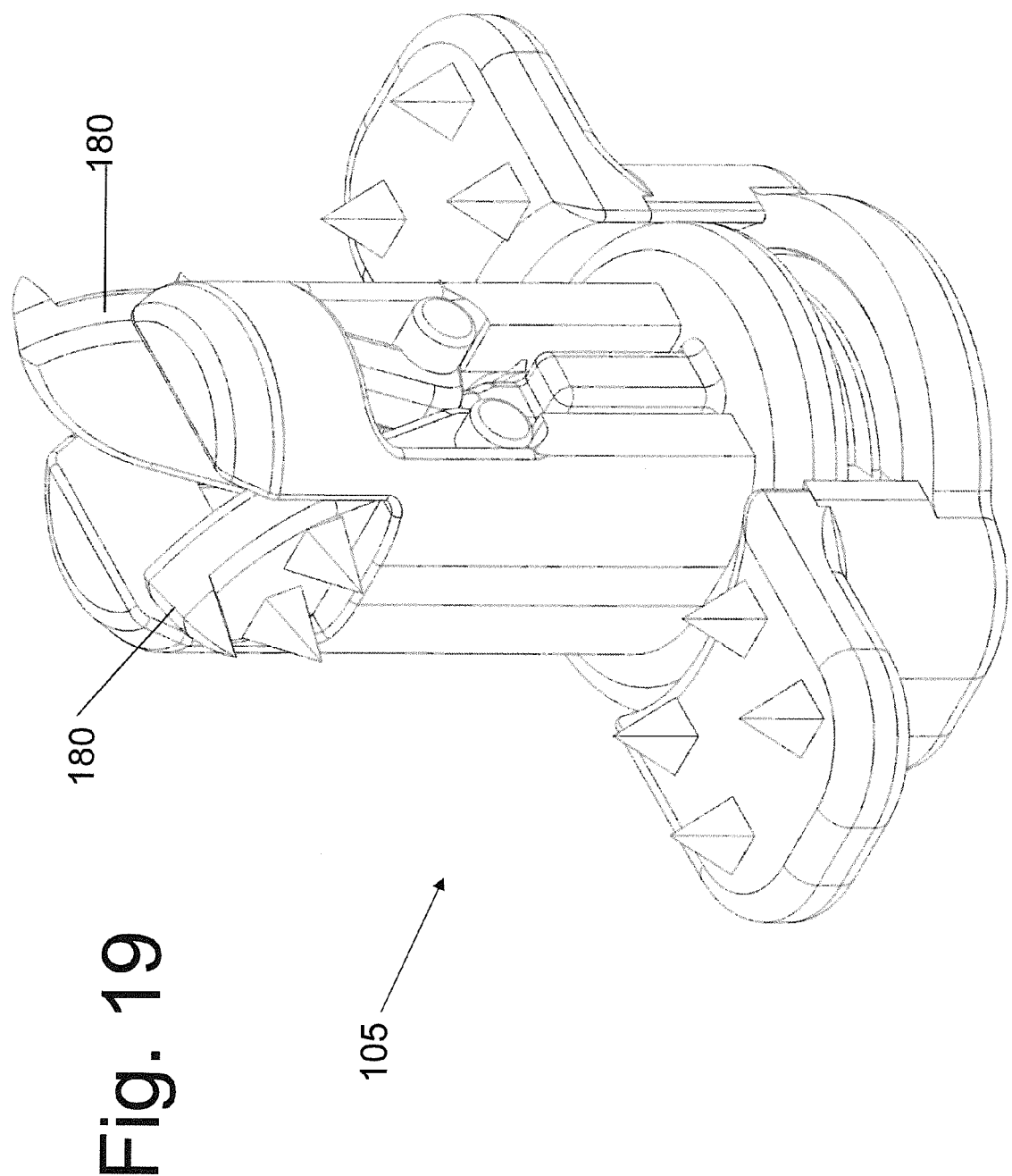
FIG. 19 illustrates a perspective view of the assembled fixation device with the arms in the partially deployed position.
Figure 20:
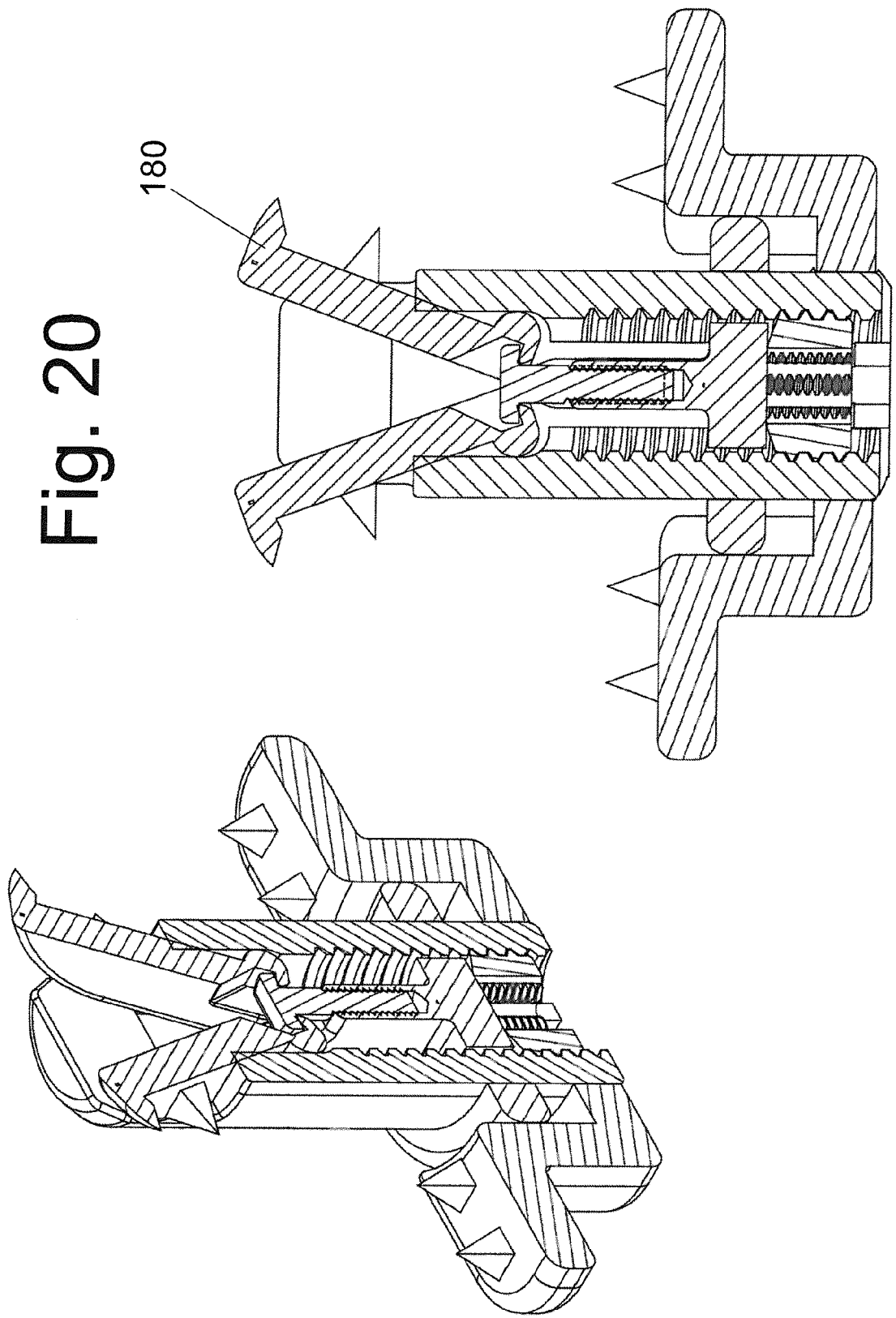
FIG. 20 illustrates cross-sectional views of the device of FIG. 19.

FIGS. 19 and 20 illustrate a cross-sectional view of a partially deployed state of an assembled fixation device 105. Member 150 is shown having been drawn partially through holes 132. Rotation arms 180 that had previously been in contact with shoulders 1646 are being translated upward through bore 154 and towards upper surfaces 1644. As member 150 is drawn through holes 132 in plate member 120, surfaces 1240 of protrusion 124 of plate 120 press against surfaces 188 of rotation arms 180 and force the rotation arms 180 upward through bore 154. Hinge element 192 travels from shoulder 1646 near a lower end of the window 164 toward the surface 1644 at the upper end of window 164. As the hinge element 192 approaches the upper end of window 164, the rotation arms 180 begin to rotate around the axis of hinge 192 such that arms 180 rotate away from one another. Once the hinge 192 of rotation arms 180 abuts the upper surface 1644 of window 164 and no translation space remains, the rotation arms 180 are urged to rotate around axis of hinge 192 and travel down into U-shaped channel 161.

Figure 21:
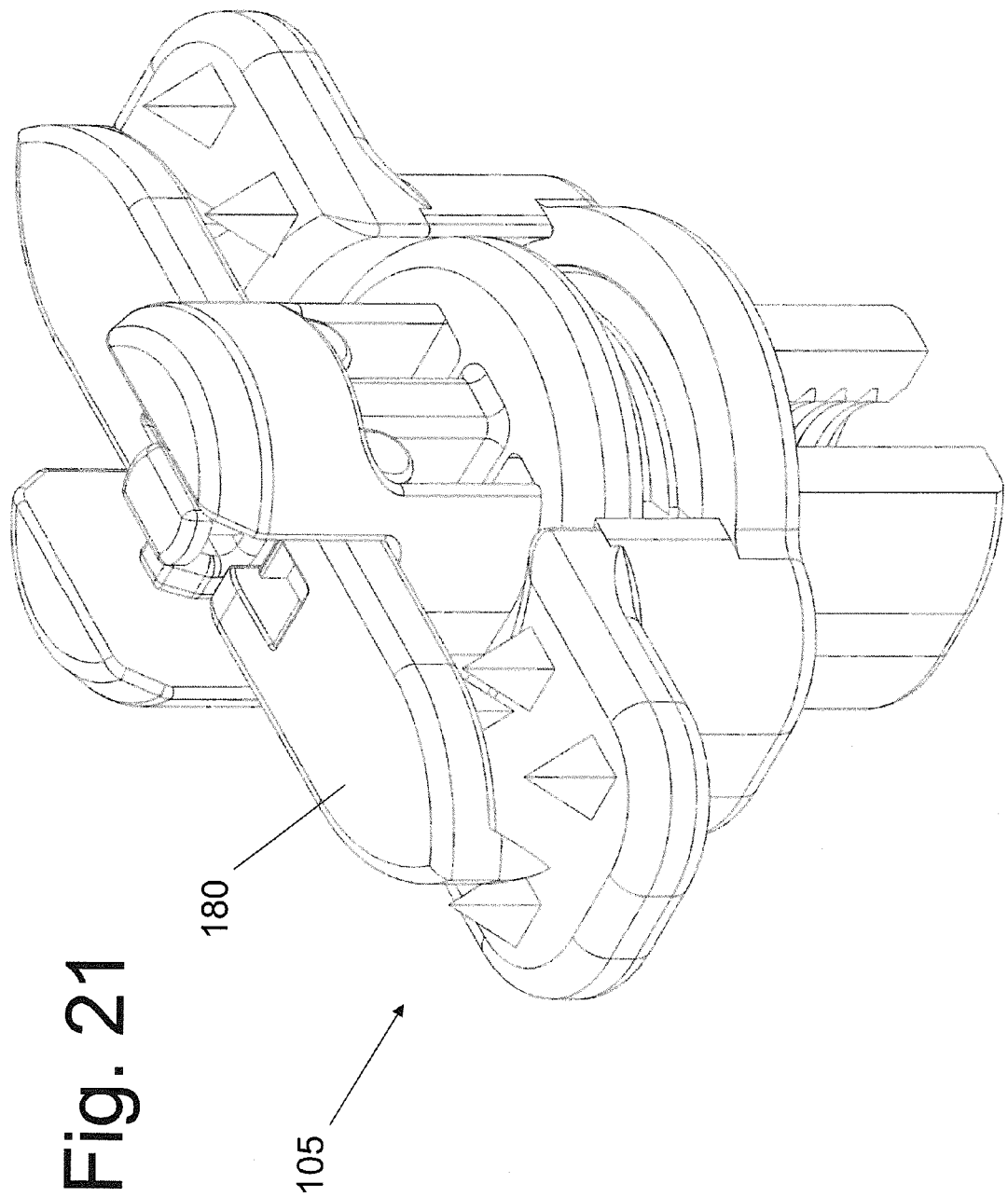
FIG. 21 illustrates a perspective view of the assembled fixation device with the arms in the fully deployed position.
Figure 22:
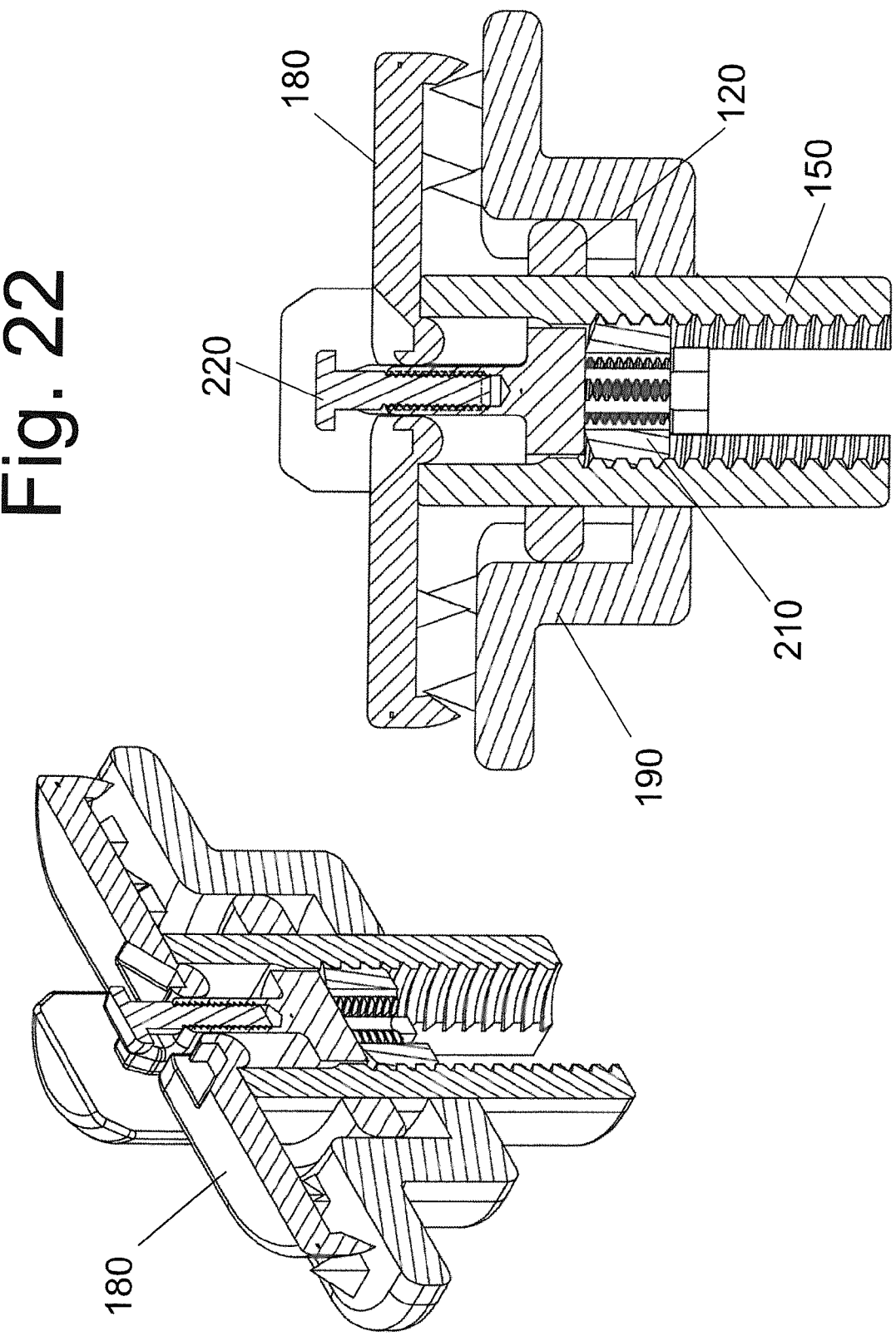
FIG. 22 illustrates cross-sectional views of the device of FIG. 21.

FIGS. 21 and 22 illustrate perspective and cross-sectional views of a fixation device 105 in the deployed state. Rotation of locking nut 210 has caused the rotation arms 180 to be forcibly rotated towards a substantially perpendicular position relative to the long axis of elements 162. The upward-extending elements 1240 of protrusion 124 abut against corners 188 of each rotation arm 180. The rotation arms 180 continue to rotate until they are in a substantially perpendicular orientation relative to the long axis of elements 162. Hinge elements 192 of rotation arms 180 at this point have fully migrated towards and now abut the upper surfaces 1644. Note that shoulder 1246 of protrusion 124 will abut surface 1648 (connecting each of the two surfaces 1644) and will prevent any further advancement of member 150 relative to plate 120.

After full deployment of the deployment arms, member 190 is then attached to device 105. Member 190 is forcibly advanced towards the deployed arms 180 so that the bone-engaging surfaces 1946 of member 190 is translated towards bone-engaging surface 183 of rotation arms 180 so as to compress and retain the side surfaces of the intervening spinous process there between. With advancement of member 190, protrusions 182 and 1944 will penetrate the sides of the intervening spinous process and increase the fixation strength of the device. Member 190 is advanced towards arms 180 by the action of a compression device and/or the threaded advancement of the locking nut 302 (see FIG. 28B). Locking nut 302 is internally threaded and adapted to engage the complimentary threads 1360 of member 136. As the locking nut 302 is rotated in a first direction, member 190 is forcibly advanced relative to member 136 and towards arms 180.

While deployment of the arms 180 have been described in detail, the arms may reversibly transition from the fully deployed configuration to the fully withdrawn configuration by rotation of locking nut 210 in the opposite direction. With reverse rotation of locking nut 210, surface 160 of member 150 moves away from nut 210. With continued reverse rotation of nut 210, screw 220 is captured in pocket 187 of rotation arms 180. Further reverse rotation of nut 210 produces forceful rotation back of rotation members 180 until the withdrawn configuration of the device (FIGS. 17 and 18) is finally achieved.

Deployment Instruments

Figure 24:
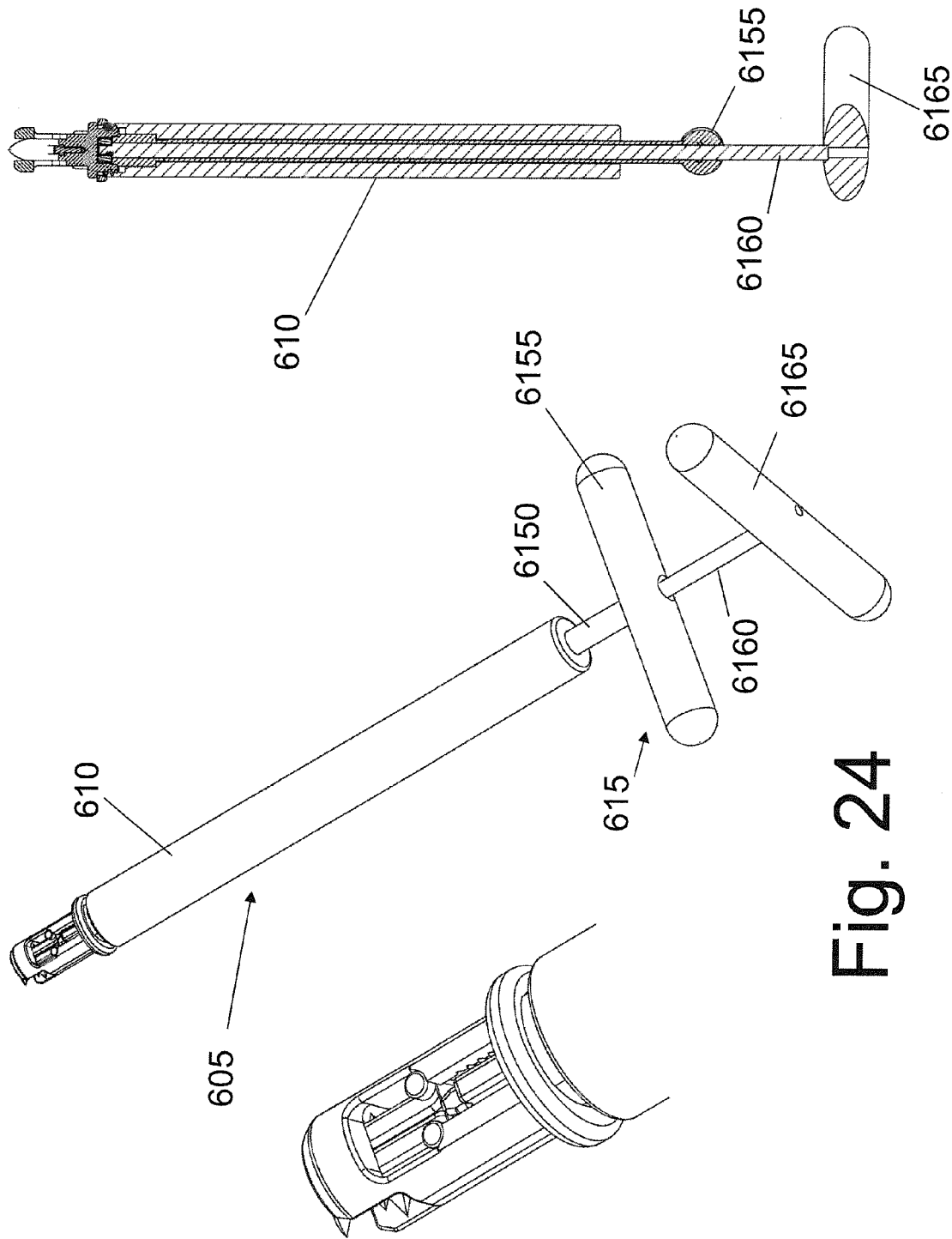

The fixation device described herein may be implanted using deployment instruments as illustrated in FIGS. 23-25, wherein device 105 may be percutaneously deployed into the inter-spinous space. The same deployment instruments 605 may be alternatively used to deliver device 105 into the inter-spinous space using minimally-invasive or conventional full open surgical techniques. Deployment instruments 605 include an elongate shaft 610 and an actuation assembly 615 extending through the elongate shaft 610. The elongate shaft 610 comprises a distal end with internal threads (not shown) configured to reversibly couple with outer threads 1360 of coupling elements 136 of the plate member 120. The deployment instrument 605 may be rigidly attached to plate member 120 upon thread engagement between shaft 610 and coupling elements 136 (see FIGS. 23-24).

The actuation assembly 615 may include an engagement member 6150 having a central bore through which an inner driver 6160 extends. Both inner engagement member 6150 and the inner driver 6160 translate independently through the shaft 610 and with respect to each other. Inner engagement member 6150 has a distal portion 6154 having protrusions 61542 and a proximal handle portion 6155. The protrusions of the distal portion 6154 snugly fit within notched inner surface 1364 of coupling element 136 of plate member 120. Handle portion 6155 is externally available outside the elongate shaft 610 and the patient such that it may be used by the operator to translate and rotate the inner engagement member 6150. Coupling inner engagement member 6150 to plate member 120 allows the operator to manipulate the position of the fixation device 105 which is positioned within the body cavity of a subject while handle 6155 is positioned outside of the body. Inner driver 6160 has a distal driver portion 6164 and a proximal handle 6165. The distal driver portion 6164 may comprise a Tor-X driver configured to engage opening 213 of nut 210 (Portion 6164 may be alternatively any other driver configuration that is adapted to mate with the complimentary nut surface). Rotation of inner driver 6160 produces rotation of locking nut 210. Handle portion 6165 may be externally available outside the elongate shaft 610 and the patient such that it may be used by the operator to rotate the inner driver 6160.

In this way, the operator holds handle 6155 in one hand outside the patient and guides implant 105 to the desired position within the patient. The implant is guided to position inside of the patient's body using radiographic imaging techniques. Once device 105 is positioned at the target interspinous space, the operator rotates handle 6165 (relative to handle 6155) with a second hand in order to transition the rotation arms of the implant 105 from the fully withdrawn configuration to the fully deployed configuration (Note that rotation member deployment is reversible, wherein reverse rotation of handle 6165 will drive the rotation arm from the deployed to the withdrawn configuration.)

In order to complete deployment of device 105, inner driver 6160 is removed from the internal bore of engagement member 6150. Exchange member 705 is then advanced into the internal bore of member 6150—as shown in FIG. 26A. Exchange member 705 (FIG. 26B) has elongated body 7052 with distal threads 7055. Threads 7055 are configured to threadedly mate with complimentary threads 215 of nut 210. With rotation of exchange member 705, the distal threads engage the complimentary internal threads 215 of nut 210. Member 610 is then dis-engaged from its threaded attachment to threads 1360 of coupling element 136. Deployment instrument 605 is removed from the inner aspect of the subject's body. However, device 105 remains positioned at the implantation position within the body cavity of the subject and the distal aspect of exchange member 705 remains threadedly attached to implant 105, wherein the proximal aspect of member 705 is positioned outside of the subject's body and available to the surgeon (see FIG. 27A). (That is, when in use, the elongated body of member 705 traverses the skin incision so that a distal segment rests within the subject and a proximal segment rests outside of the subject's body.)

Member 190 is then advanced along the length of member 705 (using placement instrument 715) until bore 1922 is seated around coupling element 136 of member 120 (see FIG. 27B). At this point, protrusions 1944 are in proximity to the ipsilateral side surface of the spinous processes that border the implanted inter-spinous space. Likewise, protrusions 182 of rotation arms 180 are in proximity to the contralateral side surface of the spinous processes. Note that member 190 may be advanced along member 705 with its longitudinal axis (i.e., an axis extending from one abutment surface to the other) substantially perpendicular to the long axis of member 705. See e.g., FIGS. 28A and 28B. However, in order to minimize the profile of member 190, it may be alternatively advanced along member 705 with its longitudinal axis positioned obliquely relative to the axis of member 705.

A nut 302 is advanced after member 190, wherein the nut 302 is internally threaded and is adapted to engage complimentary threads 1360 of member 120. With threaded advancement of nut 302, member 190 is forced towards deployed rotation arms 180. As noted, during actual use, the spinous processes to be fixated together will be positioned between the spiked surface of rotation arms 180 and the spiked surface of member 190. As nut 302 is advanced further, the spiked surface of the rotation arms 180 is forcibly advanced into the contralateral (relative to side of skin incision) side surface of each of the spinous processes of the upper and lower vertebral bones at the fixation level. Similarly, the spiked surface of member 190 is forcibly advanced into the ipsilateral side surface of each of the spinous processes of the upper and lower vertebral bones. After the nut 302 is appropriately tightened, the tightening instrument (not shown) and exchange member 705 are removed, leaving implant 105 implanted within the desired interspious space.

Methods of Use

The implantation of the fixation devices will now be described. As mentioned above, the device performs a spacing function in that member 150 rests within the target inter-spinous space and maintains the adjacent spinous processes at a desired distance from one another. The implant 105 also performs a fixation function in that the spinous processes of the implanted vertebral bones are locked in position relative to one another. These devices may be implanted using a lateral approach and that same lateral approach may be used to fixate the spinous processes of vertebral bones being treated. By positioning the implant into the desired inters-pinous space and then advancing the locking nut 210, the rotation arms 180 are urged to rotate. By forcibly advancing member 190 towards plate member 120, the implant captures and rigidly fixates the spinous processes that are adjacent to the implanted interspinous space between the rotation arms 180 and plate member 190.

It should be appreciated that the fixation device described herein may be used with any surgical approach to the posterior aspect of the spine and the disclosed fixation device may be positioned in the spine using any appropriate surgical method and/or surgical corridor. The fixation device described herein is particularly adapted to be placed through a lateral surgical approach to the spine that starts with a surgical incision in the posterior aspect of the patient's flank (i.e., side aspect of the abdominal cavity). The fixation devices described herein are also particularly adapted for use in stabilizing the posterior aspect of a spinal segment when a second orthopedic implant is implanted into the disc space of that segment using a lateral, or flank, approach to the disc space. It is noted that while the lateral approach is employed in one method of use, the implantation procedure of the device is by no means limited to a lateral approach to the interspinous space. A posterior approach or a postero-lateral approach (such as, for example a trans-formainal inter-body fusion (TLIF) approach) may be alternatively used as will be dicussed below.

Figure 6:
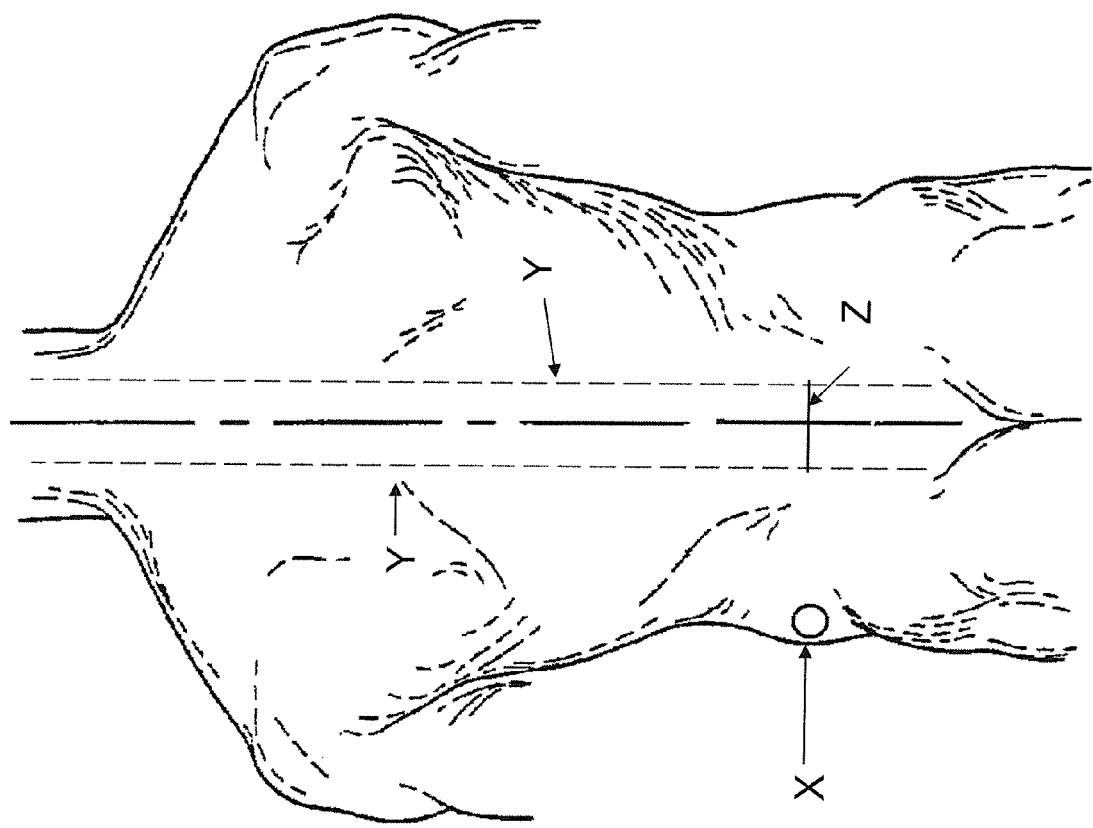
FIG. 6 is a schematic representation of the posterior aspect of a patient.

In an embodiment, the fixation devices are implanted into the lumbar spine using a flank incision and a lateral approach—which is now described. The spinal level of desired device implantation may be localized under radiographic guidance. Referring to FIG. 6, a skin incision is placed in the flank at the approximate cephalad-caudal level of the implantation site on the spine. FIG. 5 illustrates a cross sectional view of the torso at the level of the device implantation within the lumbar spine. For clarity of illustration, the contents are represented schematically and those skilled in the art will appreciate that an actual cross section of the human torso may include anatomical details not shown in FIG. 5.

In preparation for percutaneous placement of the implant into a spinal level, the patient may be, but is not necessarily, placed in a prone or lateral decubitus position. The level of the spine that is to be implanted (may be also referred to as the "operative level" or "target level") is localized using radiographic imaging techniques (X-rays, CT, MRI and the like) in at least one plane. After the customary sterile preparation of the operative site, the surgeon localizes an incision point on the skin that is substantially directly lateral to the spinal segment that will be implanted. In an embodiment, an orthopedic implant (preferably, but not necessarily, a fusion implant) is placed into the disc space of the operative level prior to implantation of the interspinous implant. (However, it is alternatively contemplated to place device 105 into the inter-spinous space prior to implantation of the disc space.)

FIG. 6 illustrates a schematic representation of the posterior aspect (i.e., back) of a subject. The skin overlying the back is shown. Lines Y depict the lateral extent of the transverse processes of the spinal column. Assuming that the spinal level to be accessed is at line Z, the surgeon makes an incision at or about circle X.

A lateral corridor "Y" (FIG. 5) is made from the flank, through the psoas muscle 116 and onto the lateral aspect of the disc space at the spinal level to be implanted. An implant may be placed through the corridor Y and into disc space or onto the spine. The procedure is known to those skilled in the art and known as the XLIF procedure (see "Extreme Lateral Interbody Fusion (XLIF): a novel surgical technique for anterior lumbar interbody fusion." By Ozgur, Aryan et al. in Spine J. 2006 July-August; 6(4):435-43, which is hereby incorporated by reference in its entirety).

A second lateral corridor "Z" (FIG. 5) may be made from the flank, through the posterior tissues lateral to the spine and onto the lateral aspect of the spinous processes and inter-spinous ligament of the level to be implanted. While Corridor Y and Corridor Z are shown schematically as exiting the skin of the flank at two different sites, both corridors may be made through a single, common skin incision on the patient's flank. Once through the skin 118, the trajectory is then varied so as to form an anatomically anterior corridor similar to Corridor Y and an anatomically posterior corridor similar to Corridor Z. The device disclosed herein is implanted into the posterior aspect of a functional spinal unit using a Corridor Z and, at the same operation, an implant is placed into or onto the anterior column (including disc space) of the same functional spinal unit using a Corridor Y.

The method of device implantation is now illustrated. In an embodiment, a functional spinal unit FSU is targeted for immobilization and fusion. (For illustration purposes, the level of implantation will be taken as the L4/5 spinal level.) FIG. 29A illustrates a spine with implant 305 positioned within the L4/L5 disc space. The level is the functional spinal unit (FSU) including the L4 and L5 vertebral bones and the intervening disc. An anterior implant 305 is placed into the L4/L5 disc space as is known in the art. For example, Implant 305 may be placed into the disc space using a lateral procedure, such as XLIF, and a lateral surgical corridor such as Corridor Y as described above with respect to FIGS. 5-6. A lateral corridor, such as Corridor Y may be used to implant fixation device 105. While the anterior implant 305 is illustrated as being implanted first, it is understood that either the anterior or posterior column implant may be positioned first. It should also be understood that a different level of the spine may be targeted for immobilization.

It is also understood that the totality of the operation—from selection of the target level to implant to the final placement of implant—may be performed under radiographic guidance. Further, the operation may be performed using percutaneous or minimally invasive surgical techniques with or without the aid of electrophysiological monitoring. The later include techniques such as electromyography (EMG) and are intended to alert the operating surgeon to the presence of nerves and other neural elements within the surgical corridor. EMG identification of nerves permits the surgeon to navigate the surgical site with increased safety and to lessen the possibility of nerve injury. (The technique is known in the art and is described in (i) Intraopertive electromyography during thoracolumbar spinal surgery. By Holland, N R. Spine 1998 Sep. 1: 23(17): 1915-22; and (ii) Improving accuracy and reducing radiation exposure in minimally invasive lumbar interbody fusion. By Wood M J, Mannion R J. J Neurosurg Spine. 2010 May; 12(5): 533-9. Each of which is hereby incorporated by reference in its entirety.)

FIG. 29B illustrates a cylindrical tissue dilator 900 placed through a lateral corridor, such as Corridor Z, to the spinous processes of L4 and L5 and the inter-spinous space between them, FIGS. 30A-30B depict the placement of a second tissue dilator 905 of greater diameter over the first tissue dilator 900. FIGS. 31A-31B illustrate the placement of a third tissue dilator 910 of still greater diameter over the second tissue dilator 905. FIGS. 32A-32B illustrate the placement of a distraction device having tubular half-receptacles 915 of greater diameter than the third tissue dilator 910. Half-receptacles 915 are advanced to the L4/L5 inter-spinous space by advancing them atop the third tissue dilator 910. After placement of receptacles 915, the tissue dilators is removed leaving a central channel 920 to the inter-spinous space (FIG. 33B). The distraction device 925 is used to distract each half receptacle 915, as shown in FIG. 32A. Note that the distraction device 925 illustrated is generic and that one of ordinary skill in art may provide other distraction devices or even sequential tissue dilatation with progressively larger tissue dilators that may produce the expanded tissue channel for device implantation. Further, each dilatation step may be checked by intraoperative radiographic imaging (x-rays, CT, MRI and the like) at the time of each tissue dilator placement. EMG may be utilized to identify nerve elements and increase procedure safety.

After the distraction platform is opened in order to further expand central channel 920, a dilator device 1005 having a tapered tip is advanced through the inter-spinous space that will be implanted. FIGS. 33A and 33B illustrate dilatation of the space between the spinous processes (inter-spinous space) and the perforation of the ligament contained therein. (Note that the posterior aspect of the inter-spinous ligament is preferentially not perforated but preserved.) This is done in preparation for device 105 implantation.

Figure 34A:
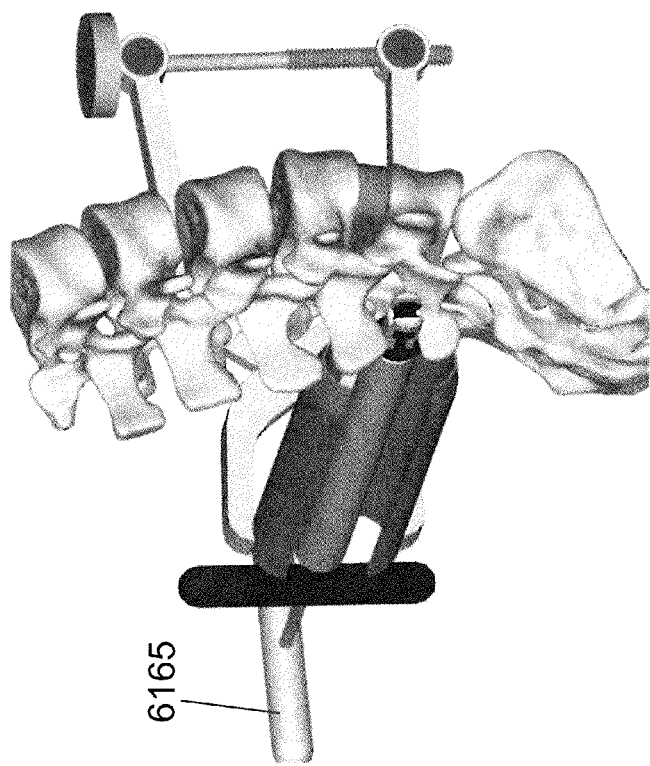
FIG. 34A illustrates the fixation device and holding instrument being advanced to the target interspinous space.

FIG. 34A illustrates the deployment instruments 605 coupled at a distal end to a fixation device 105 in the fully withdrawn state. The deployment instruments 605 and the threadedly attached fixation device 105 are then guided to the interspinous space and the distal end of the fixation device 105 is advanced through the inter-spinous space. By rotating handle 6165 and inner driver 6160, locking nut 210 is rotated and threadedly advanced so that rotation members 180 of device 105 are transitioned from the fully withdrawn state to the fully deployed state, as previously described.

Figure 34B:
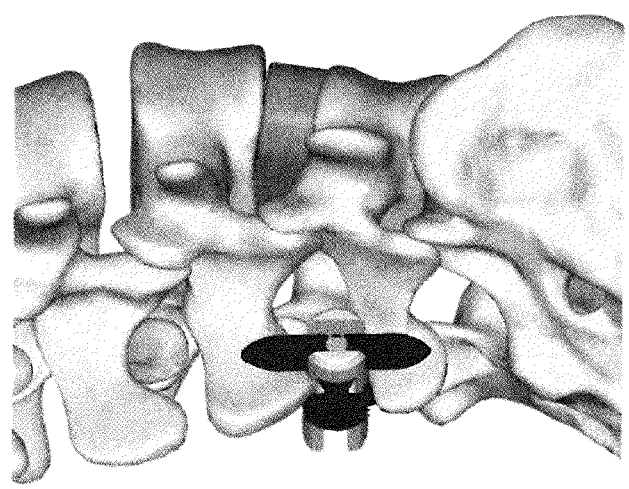
FIG. 34B illustrates the arms of the device in the fully deployed position and the deployment instrument removed.

Driver 6160 is removed from the internal bore of engagement member 6150. Exchange member 705 is then advanced into the internal bore of member 6150. Deployment instrument 605 is removed from the inner aspect of the subject's body but device 105 remains threadedly attached to exchange member 705, as described above. Member 190 is advanced along the length of member 705 and nut 302 is then advanced so as to compress the spinous processes between members 180 and 190. Member 705 is then removed from the subject leaving device 105 implanted within the subject (FIG. 34B).

Figure 35B:
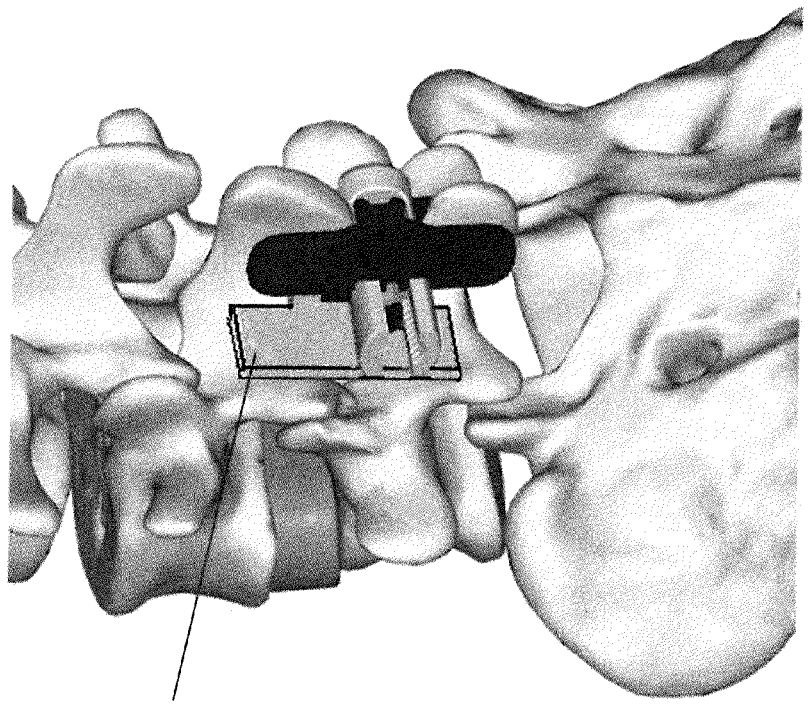
FIG. 35B illustrates the bone graft material implanted anterior to the fixation device, wherein the plate member has been implanted onto the device.
Figure 35A:
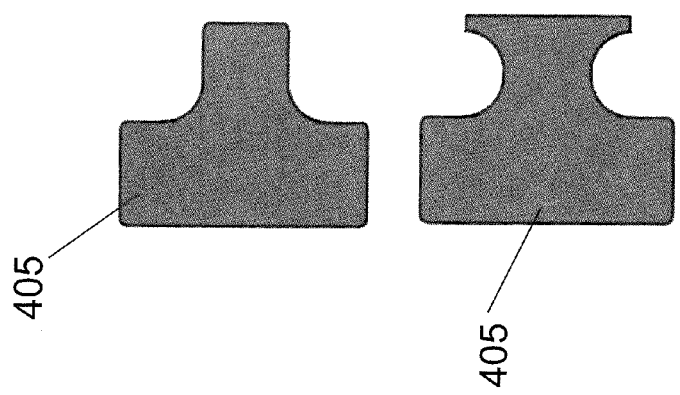
FIG. 35A illustrates exemplary embodiments of the bone graft material.

Bone graft material may be employed in the posterior column to supplement the segmental fusion provided by implant 305. FIG. 35A illustrates bone graft material 405 (which may include an allograft bone that is machined into the illustrated shapes) having a "T" or "H" shape, but it should be appreciated that other geometries are considered herein. (Additionally, or alternatively, an implant may be used wherein an implant cavity is adapted to accept a bone forming material and wherein the bone forming material of the cavity is positioned to abut and communicate with each of the two spinous process that are attached to the implant (see paragraph 0061).) In use, the posterior aspect of the L4 lamina and the posterior aspect of the L5 lamina, as well as the L4 and L5 spinous processes may be denuded of muscle and other soft tissues and the outer bony surface maybe de-corticated in preparation for acceptance of a bone graft material. Bone graft material 405 (or a fusion cage) is then placed in apposition with the posterior aspect of the lamina and aspect of the spinous process that is ipsilateral to the side of device insertion. FIG. 35B illustrates use of the graft material 405 positioned anterior to fixation device 105. Note that the bone graft material extends from the lamina and or spinous process of L4 to the lamina and/or spinous process of L5, wherein the bone graft material is adapted to form a fusion mass between the posterior bony elements of L4 and the posterior bony elements of L5.

Figure 36:
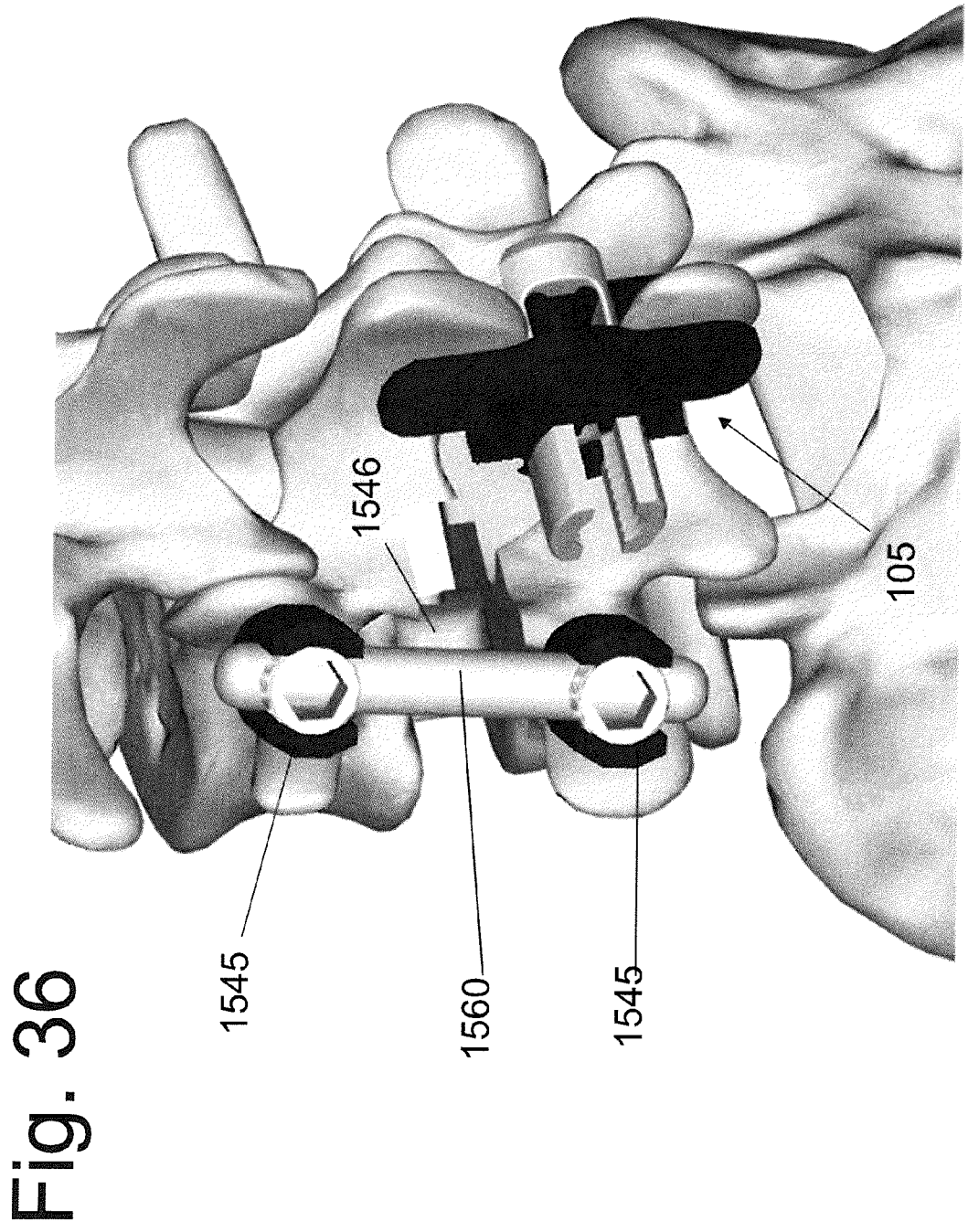
FIG. 36 illustrates use of the fixation device together with bone fixation screws that are positioned into the pedicle of the vertebral bones.

Another method of device use is shown in FIG. 36. In this embodiment, a portion of the facet joint is removed and a bone fusion implant is placed into the anterior column through the cavity created by the facet resection. This operation is known to those of ordinary skill in the art as a Transforaminal Lumbar Interbody Fusion (TLIF). A bone screw 1545 is placed into the pedicle portion of bone at each of the upper (L4 level) and lower (L5 level) vertebral bones. A rod 1560 is used to rigidly interconnect the screws 1545. The screws/rod are placed on one side of the vertebral midline and a fixation device 105 is used to supplement the uni-lateral screw/rod fixation. In one method of use, the implant 105 is implanted though the same (single) skin incision used to implant the screws 1545 and inter-connecting rod 1560, however other methods may be used with equal success.

Figure 7B:
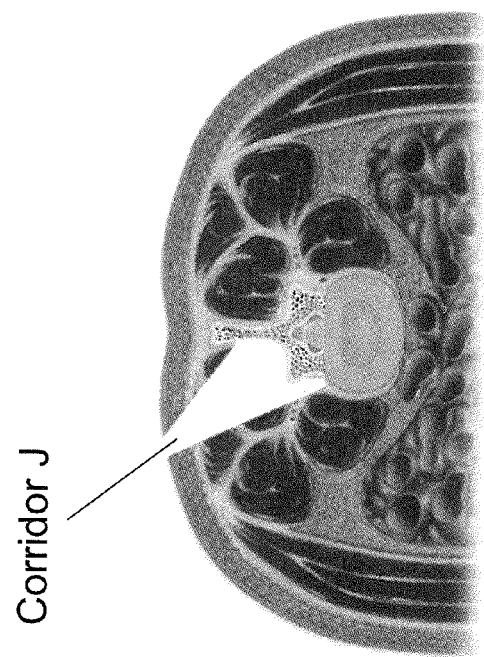
FIGS. 7A-7B are schematic representations of an implant placement corridor.
Figure 7A:
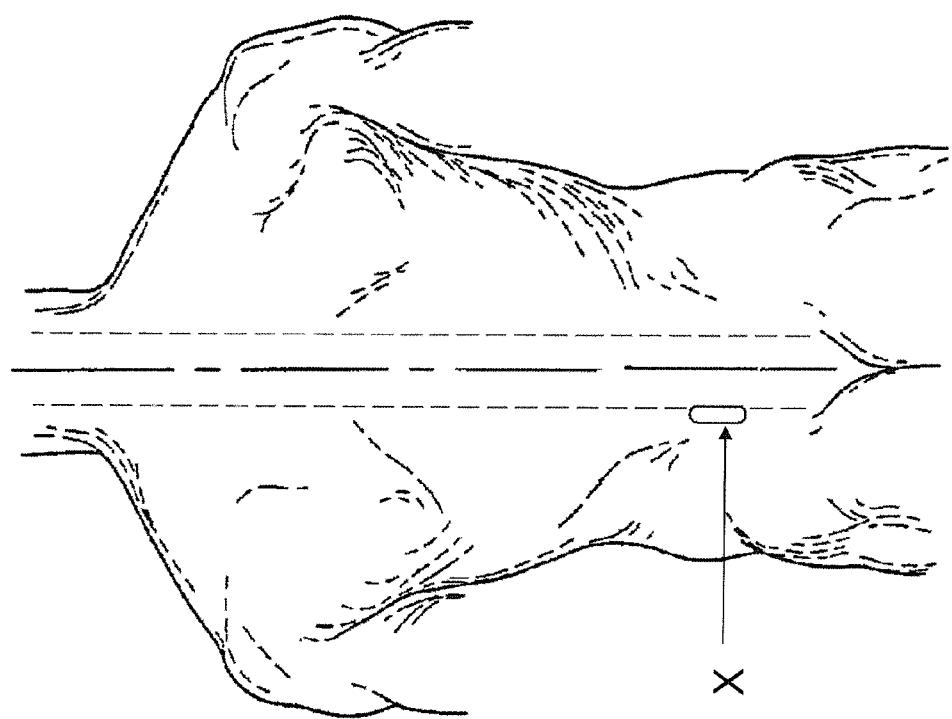

FIG. 7A illustrates a schematic illustration of the approximate location of incision site "X" for the TLIF procedure. A soft tissue corridor "J, which extends from incision "X" to the underlying bone, is shown in FIG. 7B. In a first embodiment, all implants are placed ipsilateral to the skin incision "X", wherein an implant 1546 is positioned into the disc space of the anterior column, two screws 1545 and an interconnecting rod 1560, as well as inter-spinous implant 105 are collectively delivered though corridor "J". A separate contralateral skin incision is not needed, since placement of device 105 obviates the need to place bone screws on the contralateral side of the spinous process. However, it is further contemplated that a separate skin incision may be made on the contralateral side of the spinous processes and bone screws (or other orthopedic implants) may be placed into the vertebral bones on the contralateral side of the spinous process—if the surgeon so desires.

The disclosed devices or any of their components may be made of any biologically adaptable or compatible materials. Materials considered acceptable for biological implantation are well known and include, but are not limited to, stainless steel, titanium, tantalum, combination metallic alloys, various plastics (such as PEEK and the like), resins, ceramics, biologically absorbable materials and the like. Any components may be also coated/made with osteo-conductive (such as deminerized bone matrix, hydroxyapatite, and the like) and/or osteo-inductive (such as Transforming Growth Factor "TGF-B," Platelet-Derived Growth Factor "PDGF," Bone-Morphogenic Protein "BMP," and the like) bio-active materials that promote bone formation. Further, any surface may be made with a porous ingrowth surface (such as titanium wire mesh, plasma-sprayed titanium, tantalum, porous CoCr, and the like), provided with a bioactive coating, made using tantalum, and/or helical rosette carbon nanotubes (or other carbon nanotube-based coating) in order to promote bone in-growth or establish a mineralized connection between the bone and the implant, and reduce the likelihood of implant loosening. Lastly, the system or any of its components may also be entirely or partially made of a shape memory material or other deformable material.

While this specification contains many specifics, these should not be construed as limitations on the scope of what is claimed or of what may be claimed, but rather as descriptions of features specific to particular embodiments. At a minimum, there is disclosed a device and method for vertebral fixation. The device is placed using a percutaneous (or minimally invasive) technique. The device enters a targeted inter-spinous space from a first side that is ipsilateral to the site of skin incision. At least a portion of the device is advanced across the inter-spinous space, wherein at least one first device member is rotated and/or advanced onto the contra-lateral side surface of the spinous processes that are immediately above and below the implanted interspinous space. A second device member is then also advanced onto the ipsilateral side surface of the spinous processes. In this way, the spinous processes are forcibly captured between at least the first device member on the contra-lateral side of the spinous processes and the second device member on the ipsilateral side of the spinous processes. As the locking mechanism (nut 302) is advanced further, additional force is applied by the first and second device members onto the spinous processes positioned between them. Preferably, but not necessarily, at least one protrusion extends from the first and/or second device member, wherein the protrusion is adapted to embed into the bone of a side surface of the spinous processes and increase the immobilization strength of the device.

Certain features that are described in this specification in the context of separate embodiments may also be implemented in combination in a single embodiment. Conversely, various features that are described in the context of a single embodiment may also be implemented in multiple embodiments separately or in any suitable sub-combination. Moreover, although features may be described above as acting in certain combinations and even initially claimed as such, one or more features from a claimed combination may in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

What is claimed is:

1. A method for bony fusion of a spinal segment comprising a superior vertebral bone, an immediately adjacent inferior vertebral bone and an intervening intervertebral disc space, comprising:
   identifying the spinal segment on an imaging modality;
   advancing a first orthopedic device into the intervertebral disc space using a first corridor that extends through a psoas muscle on a lateral side surface of the intervertebral disc space;
   positioning the first orthopedic device within the intervertebral disc space through the first corridor;
   advancing a second orthopedic device onto a lateral aspect of an interspinous space that is positioned between a spinous process of each of the superior and the inferior vertebral bones;
   positioning an interspinous space implant at least partially within the interspinous space, the interspinous space implant comprising:
      an elongated body that extends from a proximal end to a distal end, the body having a first surface that is configured to abut an inferior surface of the spinous process of the superior vertebral bone and a second surface that is configured to abut a superior surface of the inferior spinous process of the inferior vertebral bone, the surfaces being joined by an interconnecting wall and separated by a cavity that is configured to house a bone forming material, and to permit the formation of a bone fusion therethrough; and
      a first bone abutment member that is coupled to a distal segment of the elongated body and a second bone abutment member that is coupled to a proximal segment of the elongated body, the first bone abutment member configured to movably rotate relative to the elongated body; and
   actuating a locking feature to advance the first and the second bone abutment members towards one another and to forcibly immobilize the spinous process of each of the superior and inferior vertebral bones therebetween.

2. A method as in claim 1, wherein the acts of positioning the inter-vertebral disc space implant and the interspinous space implant occur via a single incision in the lateral skin surface of the subject.

3. A method as in claim 1, further comprising positioning the bone forming material at least partially within the target interspinous space and adjacent to the interspinous space implant.

4. A method as in claim 1, wherein the inter-vertebral disc space implant and/or the interspinous space implant is at least partially manufactured from a metallic alloy.

5. A method as in claim 1, wherein the inter-vertebral disc space implant and/or the interspinous space implant is at least partially manufactured from a plastic material.

6. A method for bony fusion of a first target vertebral bone, an immediately adjacent second target vertebral bone, and an intervening interventricular disc space, comprising:
   identifying the target vertebral bones on an imaging modality;
   placing a skin incision that is posterior and lateral to a posterior aspect of one or more pedicles of the target vertebral bones and developing a surgical corridor to an ipsilateral target facet joint, the target facet joint comprising an articulation between the first and second target vertebral bones;
   removing at least a portion of the target facet joint and advancing at least a first segment of a first orthopedic implant into the intervertebral disc space through a trans-foraminal surgical corridor;
   developing a surgical corridor to a lateral aspect of a target interspinous space, the target interspinous space being positioned between a spinous process of the first vertebral bone and a spinous process of the second vertebral bone;
   positioning an interspinous space implant within the target interspinous space, the interspinous space implant comprising:
      an elongated body that extends from a proximal end to a distal end, the body having a first surface that is configured to abut an inferior surface of a superior spinous process and a second surface that is configured to abut a superior surface of an inferior spinous process, the surfaces being joined by an interconnecting wall; and
      a first bone abutment member that is coupled to a distal segment of the elongated body and a second bone abutment member that is coupled to a proximal segment of the elongated body, the first bone abutment member configured to movably rotate relative to the elongated body, and at least one of said bone abutment surfaces configured to translate towards the other of said bone abutment surfaces;
   actuating a locking feature to advance the bone abutment members towards one another and to forcibly immobilize the inferior and superior spinous processes therebetween;
   anchoring a first into a pedicle of the first target vertebral bone, and a second bone screw into a pedicle of the second target vertebral bone; and
   connecting the first and second bone screws via a rod.

7. A method as in claim 6, wherein the acts of positioning the inter-vertebral disc implant and the interspinous space implant occur via a single skin incision.

8. A method as in claim 6, further comprising positioning the bone fusion material at least partially within the target interspinous space and adjacent to the interspinous space implant.

9. A method as in claim 6, wherein the interspinous space implant is at least partially manufactured from a metallic alloy.

10. A method as in claim 6, wherein the interspinous space implant is at least partially manufactured from a plastic material.

11. A method for anterior and posterior decompression of a spinal canal between a superior vertebral bone and an inferior vertebral bone, comprising:
- identifying a spinal level to be decompressed;
- placing a first orthopedic implant within a disc space between the superior vertebral bone and the inferior vertebral bone at an anterior column of the spinal level to be decompressed;
- rigidly immobilizing a spinous processes of the superior vertebral bone and a spinous process of the inferior vertebral bone relative to one another by:
  - advancing a second orthopedic implant into an interspinous space therebetween in a percutaneous manner; and
  - actuating a locking mechanism of the second orthopedic implant to advance a first rigid abutment surface of the second orthopedic implant towards a second rigid abutment surface of the second orthopedic implant, and to place a compressive load onto a first and a second bony surface which the first and second rigid abutment surfaces are configured to abut, respectively, the applied compressive load being sufficient to immobilize the second orthopedic implant relative to the spinous processes of the superior and inferior vertebral bones;
- anchoring a first bone screw into a pedicle of the superior vertebral bone;
- anchoring a second bone screw into a pedicle of the inferior vertebral bones; and
- connecting the first and second bone screws via a rod.

12. The method of claim 11, wherein the act of actuating the locking mechanism occurs via engagement and actuation thereof with a locking instrument.

13. The method of claim 11, further comprising placing a skin incision that is posterior and lateral to a posterior aspect of a pedicle of the superior vertebral bone and a pedicle of the inferior vertebral bone to develop a surgical corridor to an ipsilateral facet joint forming an articulation between the superior and inferior vertebral bones.

14. The method of claim 13, further comprising removing at least a portion of the ipsilateral facet joint and advancing the first orthopedic implant within the disc space through a trans-foraminal surgical corridor.

15. The method of claim 14, further comprising developing a surgical corridor to a lateral aspect of the disc space, the act of advancing the second orthopedic implant occurring via the developed surgical corridor.

16. The method of claim 11, wherein the act of placing the first orthopedic implant and advancing the second orthopedic implant occur via a single skin incision.

17. The method of claim 11, further comprising positioning bone fusion material at least partially within the interspinous space and adjacent to the first orthopedic implant.

18. The method of claim 11, wherein the first and/or second orthopedic implant is at least partially manufactured from a metallic alloy.

19. The method of claim 11, wherein the first and/or second orthopedic implant is at least partially manufactured from a plastic material.

20. A method for stabilizing a spinal segment, the spinal segment comprising a superior vertebral bone, an immediately adjacent inferior vertebral bone and an intervening intervertebral disc space, the method comprising:
- identifying the spinal segment using an imaging modality;
- advancing a first orthopedic device into the intervertebral disc space via a first corridor that extends through a psoas muscle on a lateral side surface of the intervertebral disc space;
- guiding the first orthopedic device through the psoas muscle using a nerve monitoring modality;
- implanting the first orthopedic device at least partially within the intervertebral disc space;
- advancing a second orthopedic device via a second corridor that extends onto a lateral aspect of the interspinous space, the second corridor being ipsilateral to the first corridor; and
- implanting the second orthopedic device at least partially within the interspinous space, the second orthopedic device comprising:
  - a body configured to extend from a proximal segment to a distal segment and having a first surface that is configured to abut an inferior surface of a spinous process of the superior vertebral bone and a second surface that is configured to abut a superior surface of a spinous process of the inferior vertebral bone, the first and second surfaces being connected by an interconnecting wall; and
  - at least a first and a second bone abutment member coupled to the interconnecting wall, each of the first and second bone abutment surfaces comprising at least a bone penetrating feature extending therefrom and configured to anchor onto bone;
- wherein the act of implanting the second orthopedic device at least partially within the interspinous space comprises:
  - advancing the first bone abutment member onto a lateral side aspect of the spinous process of the superior vertebral bone, ipsliateral to the second corridor;
  - advancing the second bone abutment member onto a lateral side aspect of the spinous process of the inferior vertebral bone, ipsliateral to the second corridor;
  - anchoring the bone penetrating features of the first and second bone abutment members into the spinous process of the superior vertebral bone and the inferior vertebral bone, respectively; and
  - immobilizing the spinous process of the first vertebral bone relative to the spinous process of the second vertebral bone.

21. A method for stabilizing a spinal segment, the spinal segment comprising a superior vertebral bone, an immediately adjacent inferior vertebral bone and an intervening intervertebral disc space, the method comprising:
- identifying the spinal segment using an imaging modality;
- advancing a first orthopedic device into the intervertebral disc space via a first corridor that extends through a psoas muscle on a lateral side surface of the intervertebral disc space;
- guiding the first orthopedic device through the psoas muscle using a nerve monitoring modality;
- implanting the first orthopedic device at least partially within the intervertebral disc space;
- advancing a second orthopedic device via a second corridor that extends onto a lateral aspect of the interspinous space, the second corridor being ipsilateral to the first corridor; and
- implanting the second orthopedic device at least partially within the interspinous space, the second orthopedic device comprising:
  - an elongated body configured to extend along a first axis from a proximal segment to a distal segment and having a first surface that is configured to abut an inferior surface of a spinous process of the superior vertebral bone and a second surface that is configured to abut a superior surface of a spinous process of the inferior vertebral bone, the first and second surfaces being connected by an interconnecting wall;

a first bone abutment member configured to extend along a second axis and coupled to a distal segment of the elongated body, the first bone abutment member being configured to rotate relative to the elongated body and to vary an angle between the first and second axes; and a second bone abutment member that is coupled to a proximal segment of the elongated body, the second bone abutment member comprising a locking feature configured to move the first and second bone abutment members toward one another;

wherein the act of implanting the second orthopedic device at least partially within the interspinous space comprises:

rotating the first bone abutment member relative to the elongated body, the rotation advancing the first bone abutment member onto a lateral side aspect of the spinous process of the superior vertebral bone contralateral to the second corridor; and actuating the locking feature to advance the first and second bone abutment members towards one another and to immobilize the spinous process of the superior vertebral bone therebetween.

* * * * *